US012575792B2

(12) United States Patent
Sannelli et al.

(10) Patent No.: US 12,575,792 B2
(45) Date of Patent: Mar. 17, 2026

(54) DENOISING SENSED SIGNALS FROM ARTIFACTS FROM CARDIAC SIGNALS

(71) Applicant: Medtronic, Inc., Minneapolis, MN (US)

(72) Inventors: Claudia Sannelli, Berlin (DE); Eric J. Panken, Edina, MN (US); Mirko de Melis, Maastricht (NL); Gaetano Leogrande, Maastricht (NL); Scott R. Stanslaski, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1044 days.

(21) Appl. No.: 17/690,045

(22) Filed: Mar. 9, 2022

(65) Prior Publication Data

US 2022/0287646 A1    Sep. 15, 2022

Related U.S. Application Data

(60) Provisional application No. 63/160,357, filed on Mar. 12, 2021.

(51) Int. Cl.
| | |
|---|---|
| *A61B 5/00* | (2006.01) |
| *A61B 5/318* | (2021.01) |
| *A61B 5/369* | (2021.01) |

(52) U.S. Cl.
CPC .......... *A61B 5/7217* (2013.01); *A61B 5/0031* (2013.01); *A61B 5/7246* (2013.01); *A61B 5/318* (2021.01); *A61B 5/369* (2021.01)

(58) Field of Classification Search
CPC ... A61B 5/7217; A61B 5/0031; A61B 5/7246; A61B 5/318; A61B 5/369; A61B 5/4064;
(Continued)

(56) References Cited

U.S. PATENT DOCUMENTS

| | | |
|---|---|---|
| 9,294,074 B2 | 3/2016 | Brockway |
| 9,717,439 B2 | 8/2017 | Giftakis et al. |

(Continued)

OTHER PUBLICATIONS

Dora, C., & Biswal, P. K. (2019). Correlation-based ECG artifact correction from single channel EEG using modified variational mode decomposition. Computer Methods and Programs in Biomedicine, 183, 105092 (Year: 2019).*

(Continued)

*Primary Examiner* — Jennifer Robertson
*Assistant Examiner* — Elina Sohyun Jang
(74) *Attorney, Agent, or Firm* — Shumaker & Sieffert, P.A.

(57) ABSTRACT

A method for artifact suppression in a sensed signal includes receiving the sensed signal sensed in a brain of a patient, wherein the sensed signal includes a neural signal and artifacts from a cardiac signal, decomposing the sensed signal into a plurality of components of the sensed signal, determining a first group of components, from the plurality of components, that are correlated with one another, determining an estimate of the cardiac signal based on the first group of components, wherein the estimate of the cardiac signal includes the cardiac signal and components of the neural signal, and generating a denoised neural signal based on the estimate of the cardiac signal and a second group of components of the plurality of components of the sensed signal, wherein the cardiac signal is suppressed in the denoised neural signal, and wherein the second group of components excludes the first group of components.

23 Claims, 21 Drawing Sheets

(58) Field of Classification Search

CPC ....... A61B 2505/09; A61B 5/352; A61B 5/37; A61B 5/384; A61B 5/4848; A61B 5/686; A61B 5/7203; A61B 5/31

See application file for complete search history.

(56) References Cited

U.S. PATENT DOCUMENTS

| | | | |
|---|---|---|---|
| 10,857,358 B2 | 12/2020 | Bouton et al. | |
| 2019/0232066 A1* | 8/2019 | Lim | A61N 1/3754 |
| 2019/0290912 A1* | 9/2019 | Raike | A61B 5/31 |
| 2020/0338350 A1 | 10/2020 | Panken et al. | |

OTHER PUBLICATIONS

Ajay Kumar Maddirala et al., "Separation of Sources From Single-Channel EEG Signals Using Independent Component Analysis", IEEE Transactions on Instrumentation and Measurement, vol. 67, No. 2, Feb. 2018, 12 pp.

Chinmayee Dora et al., "Correlation-based ECG Artifact Correction from Single Channel EEG using Modified Variational Mode Decomposition", Computer Methods and Programs in Biomedicine, vol. 183, No. C, Jan. 2020, 11 pp.

Hui Zou et al., "Regularization and Variable Selection via the Elastic Net", Journal of the Royal Statistical Society. Series B (Statistical Methodology), vol. 67, No. 2, Mar. 9, 2005, pp. 301-320.

K. J. Lee et al., "Elimination of ECG Artifacts from a Single-Channel EEG Using Sparse Derivative Method", 2015 IEEE International Conference on Systems, Man, and Cybernetics, Oct. 2015, pp. 2384-2389.

M.P.S. Chawla, "PCA and ICA processing methods for removal of artifacts and noise in electrocardiograms: A survey and comparison", Applied Soft Computing, vol. 11, No. 2, Mar. 2011, pp. 2216-2226.

Xiaoran Ning et al., "ECG Enhancement and QRS Detection Based on Sparse Derivatives", Biomedical Signal Processing and Control, vol. 8, No. 6, Jul. 2013, pp. 713-723.

Sannelli et al., "Denoising Local Field Potentials from Electrocardiogramartifacts [abstract]", Mov Disord., vol. 36, Sep. 2021, pp. S572-S573.

Piña-Fuentes et al., "Acute Effects of Adaptive Deep Brain Stimulation in Parkinson's Disease", Brain Stimulat., vol. 13, No. 6, Nov. 2020, p. 1507-1516.

Sorkhabi et al., "Physiological Artifacts and the Implications for Brain-Machine-Interface Design", IEEE International Conference on Systems, Man, and Cybernetics (SMC), Oct. 2020, pp. 1498-1504.

* cited by examiner

104

400H

400J

400G

400I

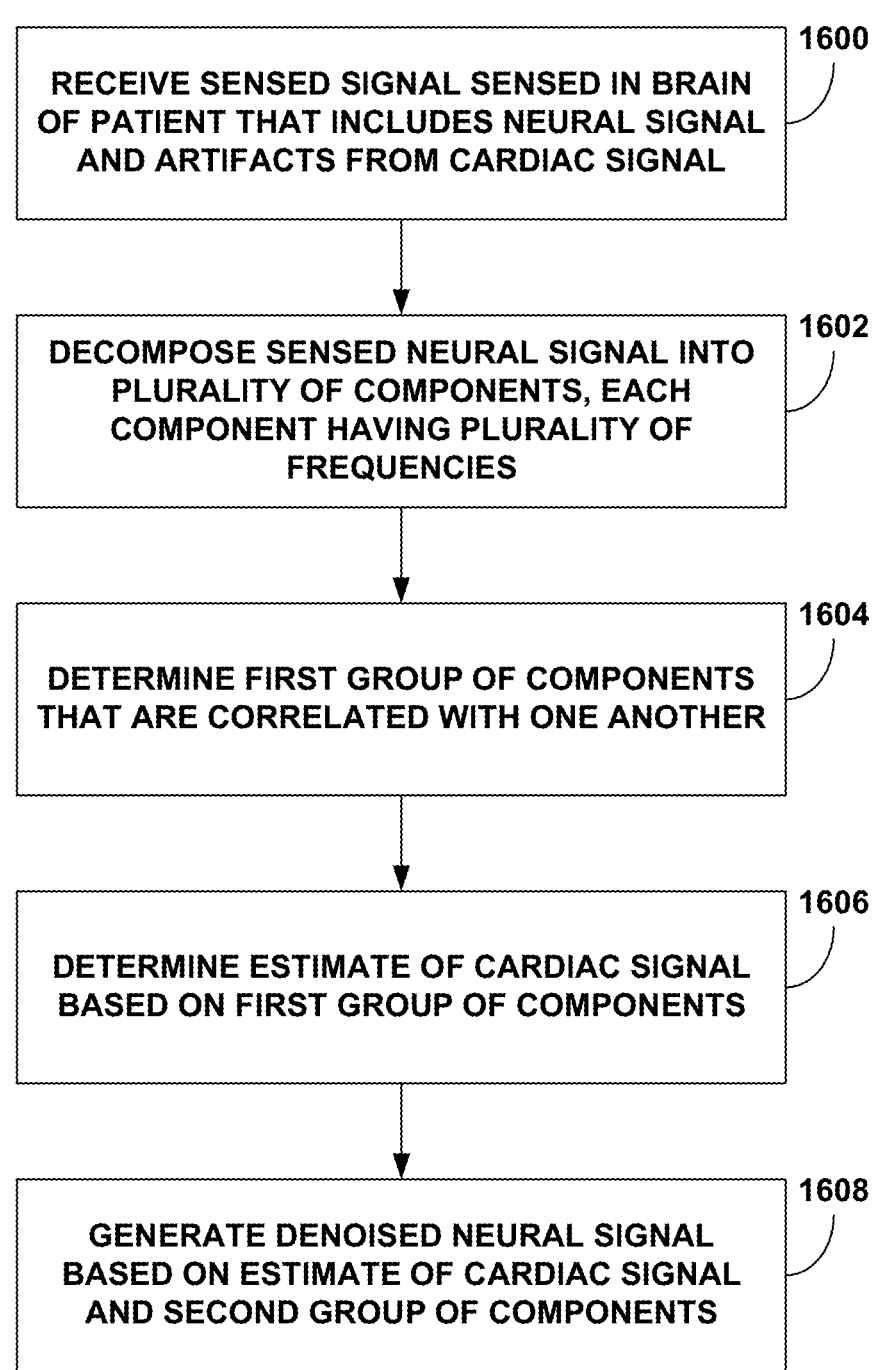

RECEIVE SENSED SIGNAL SENSED IN BRAIN OF PATIENT THAT INCLUDES NEURAL SIGNAL AND ARTIFACTS FROM CARDIAC SIGNAL          1600

DECOMPOSE SENSED NEURAL SIGNAL INTO PLURALITY OF COMPONENTS, EACH COMPONENT HAVING PLURALITY OF FREQUENCIES          1602

DETERMINE FIRST GROUP OF COMPONENTS THAT ARE CORRELATED WITH ONE ANOTHER          1604

DETERMINE ESTIMATE OF CARDIAC SIGNAL BASED ON FIRST GROUP OF COMPONENTS          1606

GENERATE DENOISED NEURAL SIGNAL BASED ON ESTIMATE OF CARDIAC SIGNAL AND SECOND GROUP OF COMPONENTS          1608

FIG. 16

DENOISING SENSED SIGNALS FROM ARTIFACTS FROM CARDIAC SIGNALS

This application claims the benefit of U.S. Provisional Patent Application No. 63/160,357, filed Mar. 12, 2021, the entire contents of which is incorporated herein by reference.

TECHNICAL FIELD

This disclosure generally relates to electrical stimulation and recording.

BACKGROUND

Medical devices may be external or implanted, and may be used to deliver electrical stimulation therapy to various tissue sites of a patient to treat a variety of symptoms or conditions such as chronic pain, tremor, Parkinson's disease, other movement disorders, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Hence, electrical stimulation may be used in different therapeutic applications, such as deep brain stimulation (DBS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes for delivery of the stimulation, a polarity of each selected electrode, a voltage or current amplitude, a pulse width, and a pulse frequency as stimulation parameters. A set of parameters, such as a set including electrode combination, electrode polarity, voltage or current amplitude, pulse width and pulse rate, may be referred to as a program in the sense that they define the electrical stimulation therapy to be delivered to the patient.

SUMMARY

In general, the disclosure describes devices, systems, and techniques for denoising sensed signals to reduce or remove artifacts from cardiac signals. As one example, one or more electrodes implanted in a brain of a patient may sense neural signals, such as local field potentials (LFPs) in the brain. However, there may be noise on the sensed signals due to the cardiac signals, such as electrocardiography (ECG) signals.

This disclosure describes example techniques to identify components in the sensed signals that are due to the cardiac signal, and suppress the identified components of the cardiac signal. As described in more detail, the example techniques may exploit the periodic nature of cardiac signals as a way in which to identify components in the sensed signals that are due to the cardiac signal to then suppress the cardiac signal in the sensed signal. In this way, the example techniques may improve the operation of sensing of neural signals, which results in better operation of a medical device that utilizes the sensed signals for diagnosis, analysis, and/or therapy delivery.

In one example, the disclosure describes a method for artifact suppression in a sensed signal, the method comprising: receiving, with processing circuitry, the sensed signal sensed in a brain of a patient, wherein the sensed signal includes a neural signal and artifacts from a cardiac signal; decomposing, with the processing circuitry, the sensed signal into a plurality of components of the sensed signal, each component having a plurality of frequencies; determining, with the processing circuitry, a first group of components, from the plurality of components of the sensed signal, that are correlated with one another, the first group of components including two or more components of the sensed signal; determining, with the processing circuitry, an estimate of the cardiac signal based on the first group of components, wherein the estimate of the cardiac signal includes the cardiac signal and components of the neural signal; and generating, with the processing circuitry, a denoised neural signal based on the estimate of the cardiac signal and a second group of components of the plurality of components of the sensed signal, wherein the cardiac signal is suppressed in the denoised neural signal, and wherein the second group of components excludes the first group of components.

In one example, the disclosure describes a system for artifact suppression in a sensed signal, the system comprising: memory; and processing circuitry coupled to the memory and configured to: receive the sensed signal sensed in a brain of a patient, wherein the sensed signal includes a neural signal and artifacts from a cardiac signal; decompose the sensed signal into a plurality of components of the sensed signal, each component having a plurality of frequencies; determine a first group of components, from the plurality of components of the sensed signal, that are correlated with one another, the first group of components including two or more components of the sensed signal; determine an estimate of the cardiac signal based on the first group of components, wherein the estimate of the cardiac signal includes the cardiac signal and components of the neural signal; and generate a denoised neural signal based on the estimate of the cardiac signal and a second group of components of the plurality of components of the sensed signal, wherein the cardiac signal is suppressed in the denoised neural signal, and wherein the second group of components excludes the first group of components.

In one example, the disclosure describes a computer-readable storage medium comprising instructions that when executed cause one or more processors to: receive a sensed signal sensed in a brain of a patient, wherein the sensed signal includes a neural signal and artifacts from a cardiac signal; decompose the sensed signal into a plurality of components of the sensed signal, each component having a plurality of frequencies; determine a first group of components, from the plurality of components of the sensed signal, that are correlated with one another, the first group of components including two or more components of the sensed signal; determine an estimate of the cardiac signal based on the first group of components, wherein the estimate of the cardiac signal includes the cardiac signal and components of the neural signal; and generate a denoised neural signal based on the estimate of the cardiac signal and a second group of components of the plurality of components of the sensed signal, wherein the cardiac signal is suppressed in the denoised neural signal, and wherein the second group of components excludes the first group of components.

The details of one or more examples of the techniques of this disclosure are set forth in the accompanying drawings and the description below. Other features, objects, and advantages of the techniques will be apparent from the description and drawings, and from the claims.

configured to deliver DBS to a patient according to an example of the techniques of the disclosure.

Figure 1:
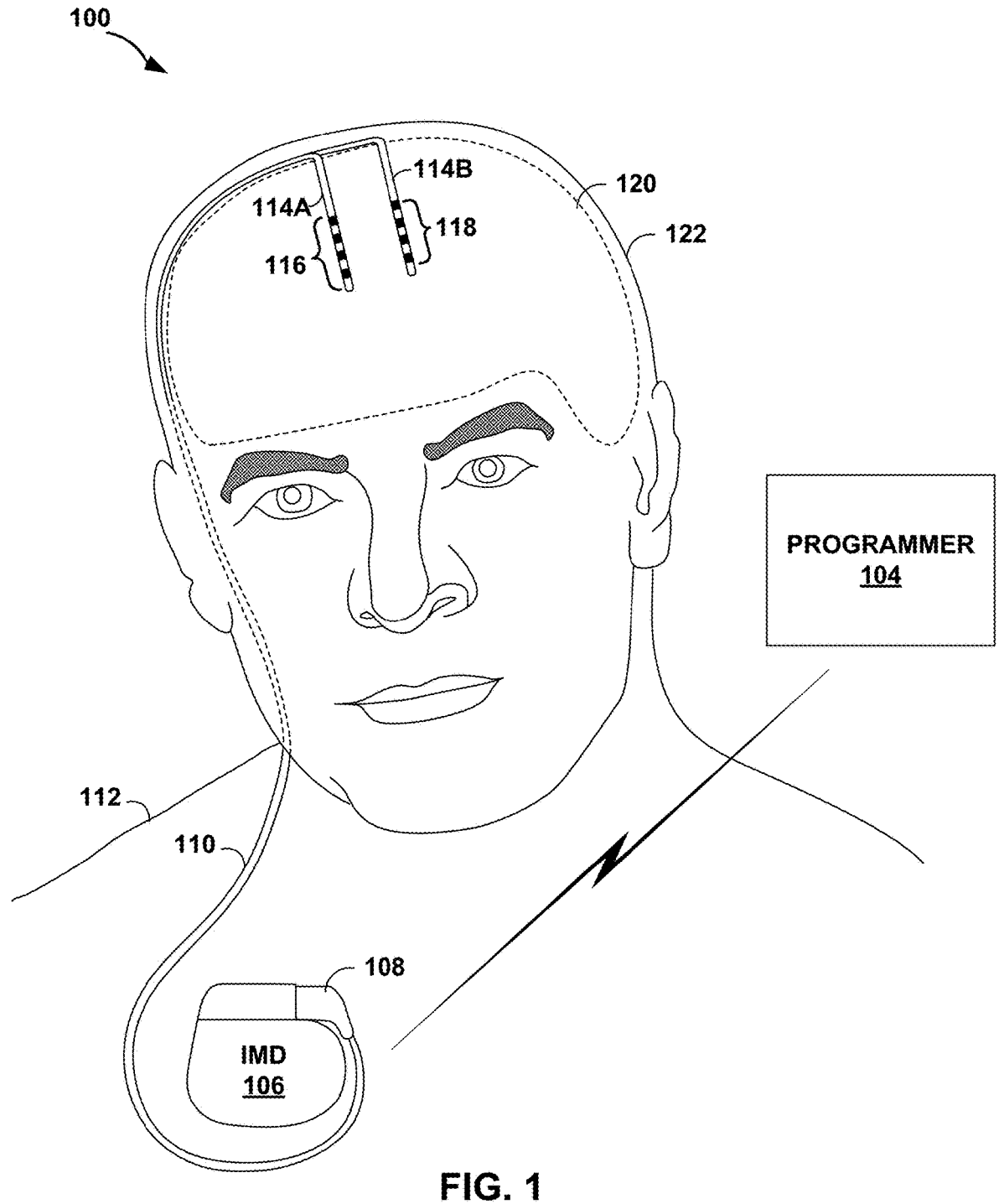
FIG. 1 is a conceptual diagram illustrating an example system that includes an implantable medical device (IMD)
Figure 2:
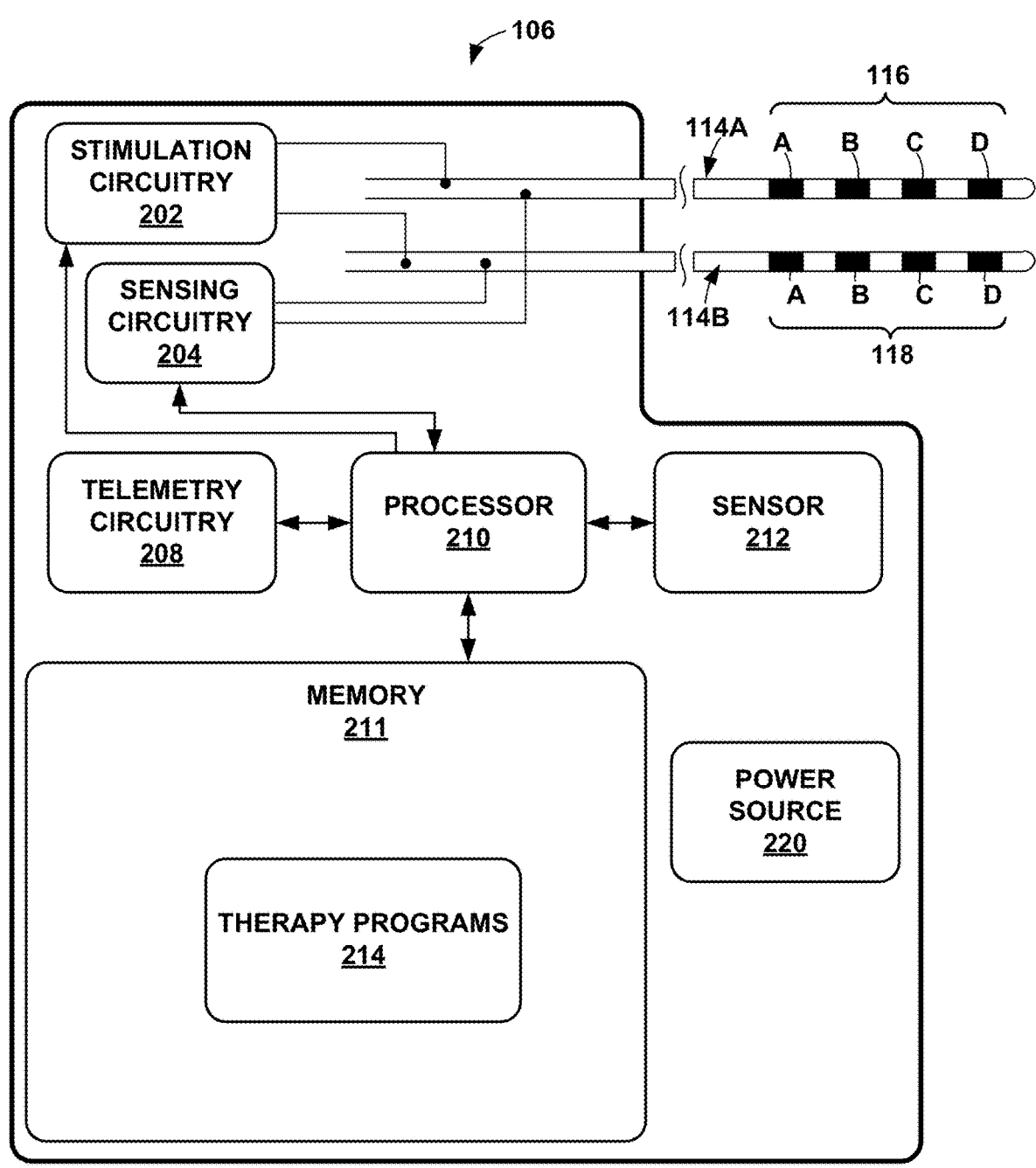

FIG. 2 is a block diagram of the example IMD of FIG. 1 for delivering DBS therapy according to an example of the techniques of the disclosure.

Figure 3:
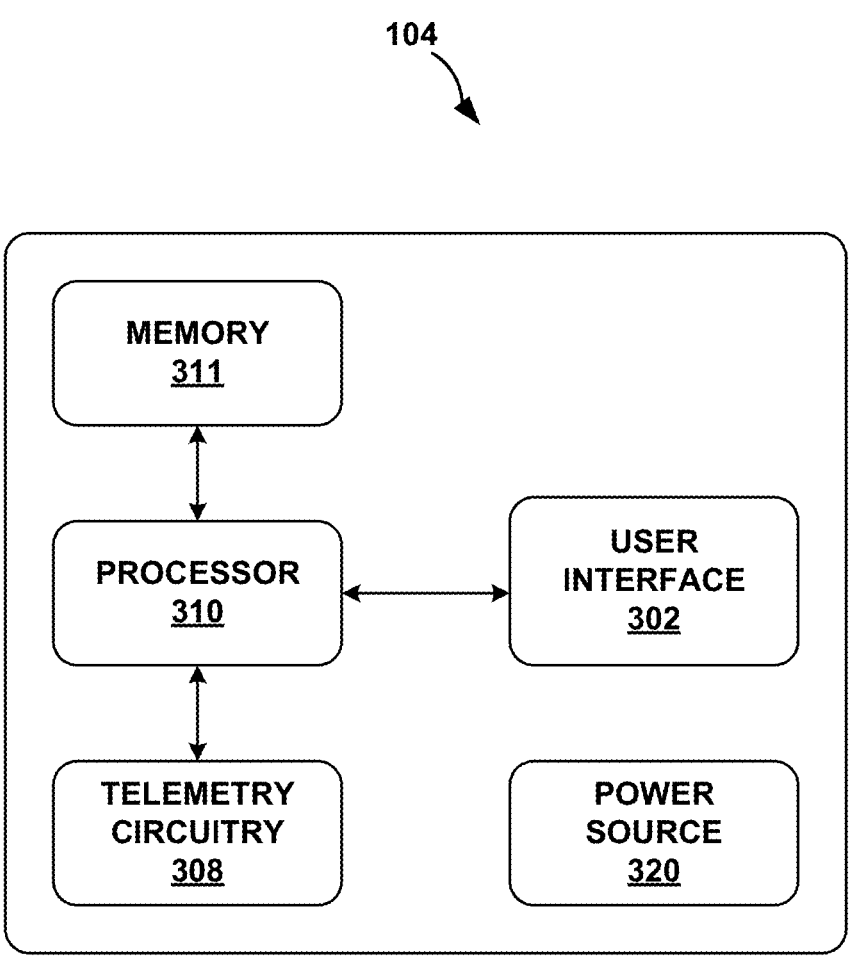
Figures 4A, 4B, 4C, 4D, 4E, 4F:
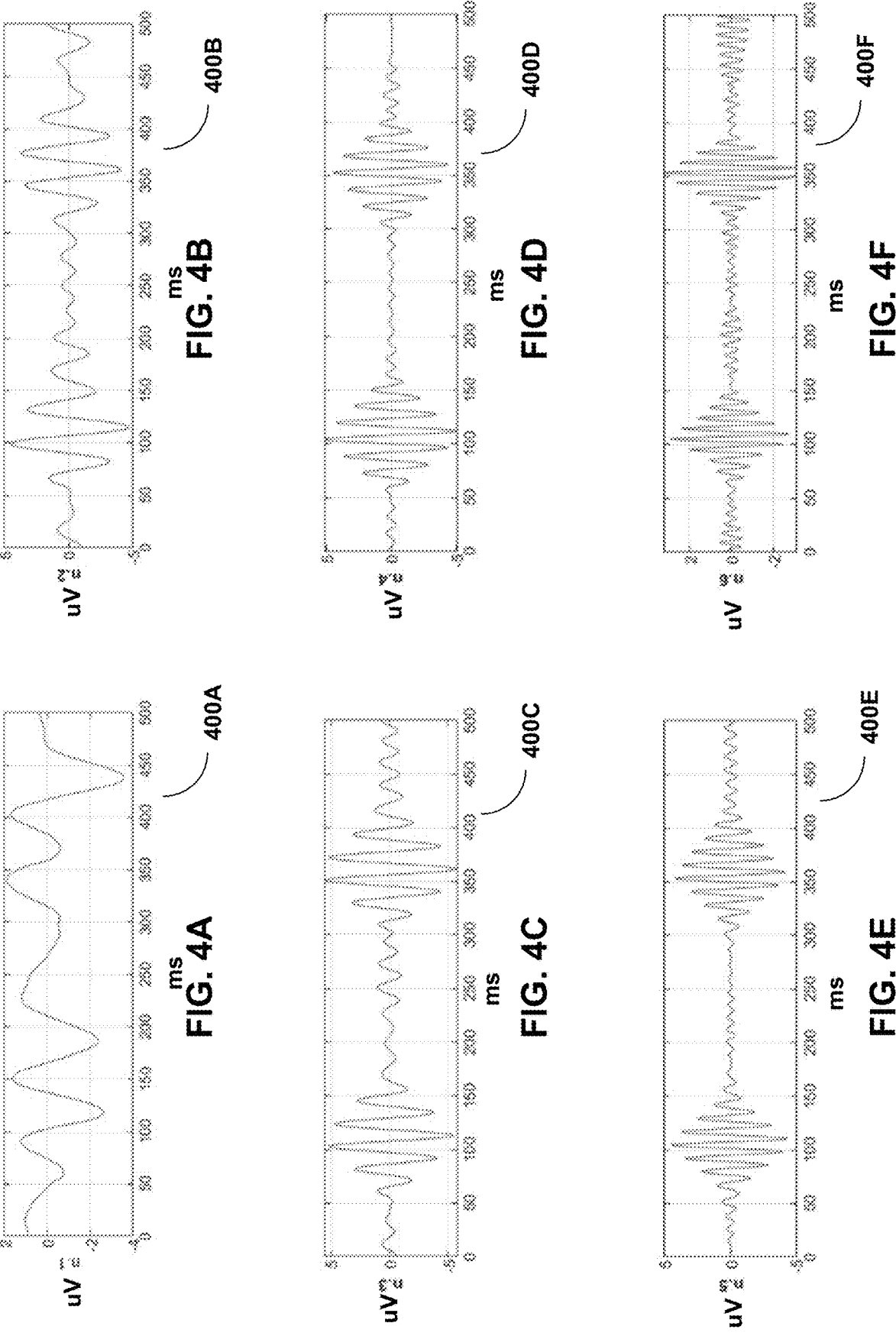
Figure 4H:
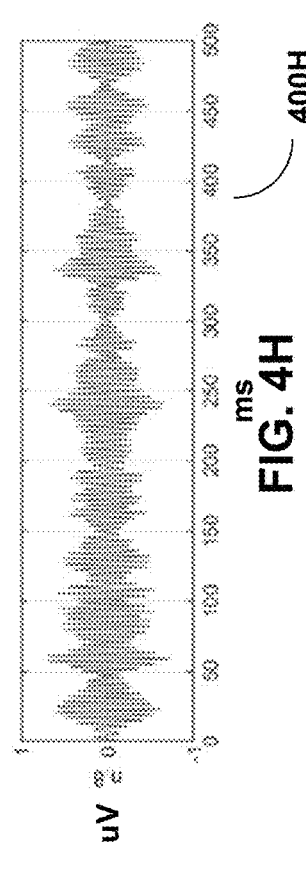
Figure 4J:
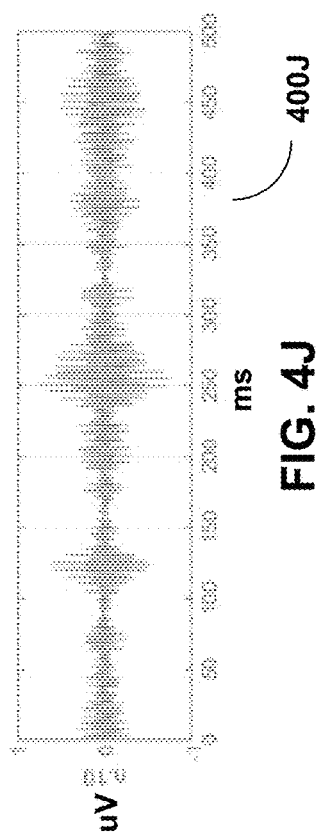
Figure 4G:
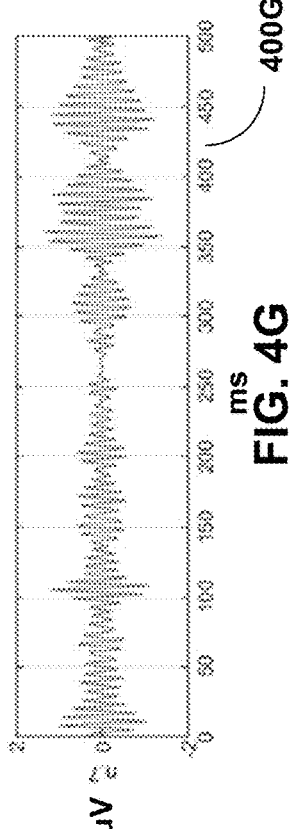
Figure 4I:
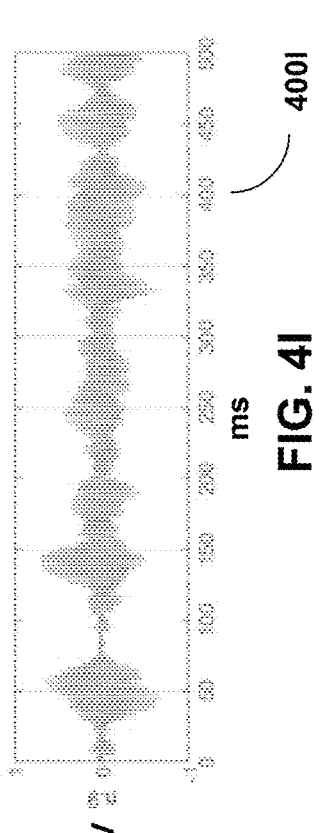
Figure 5B:
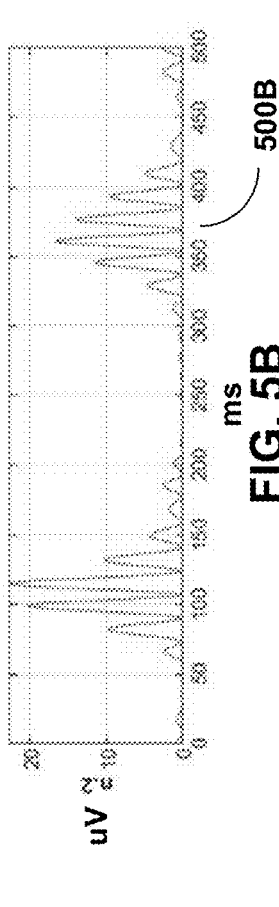
Figure 5D:
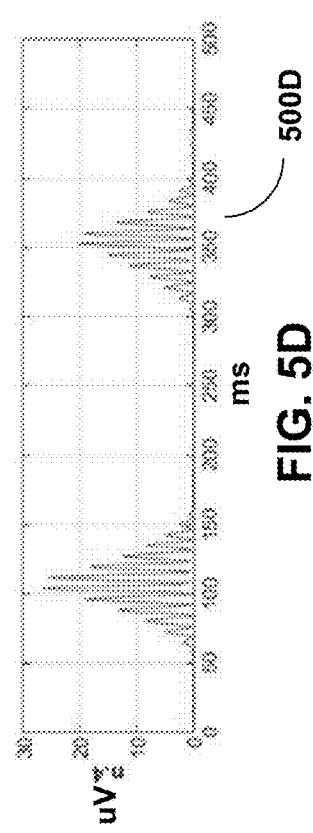
Figure 5F:
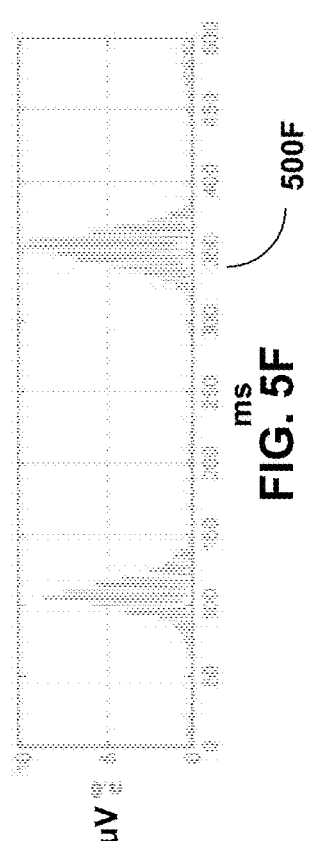
Figure 5A:
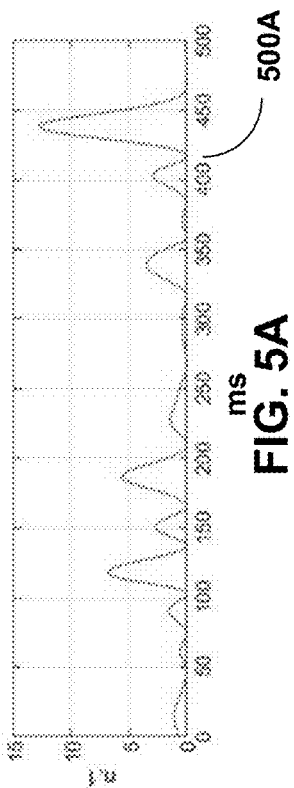
Figure 5C:
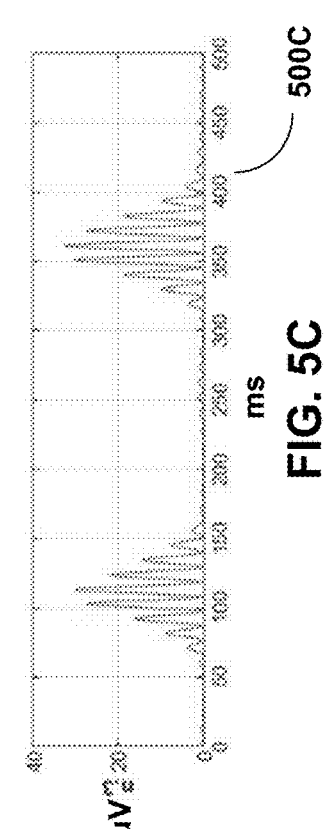
Figure 5E:
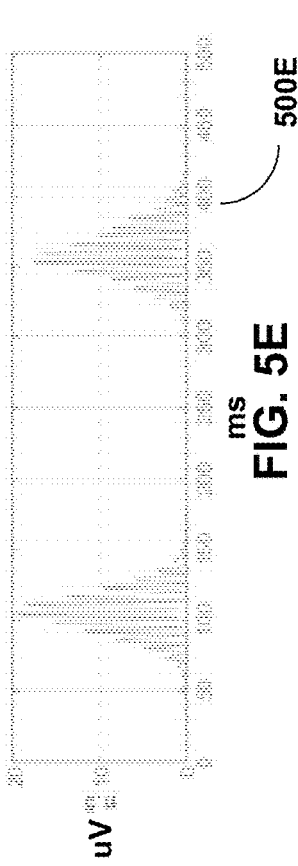
Figure 5H:
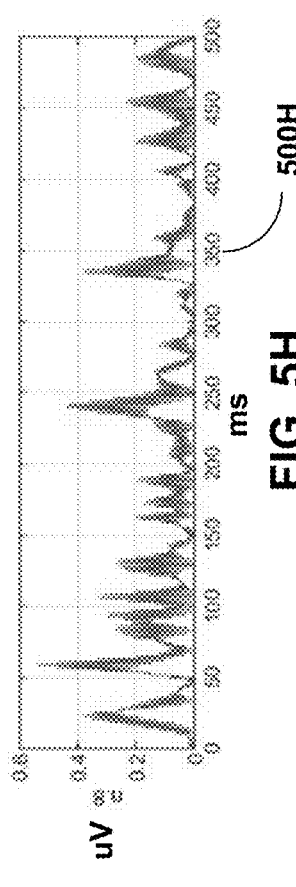
Figure 5J:
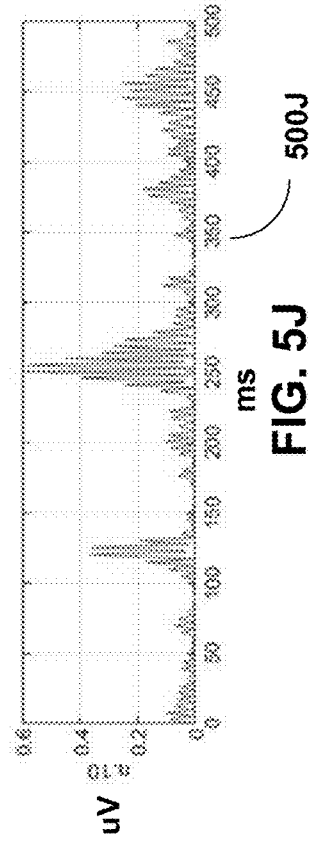
Figure 5G:
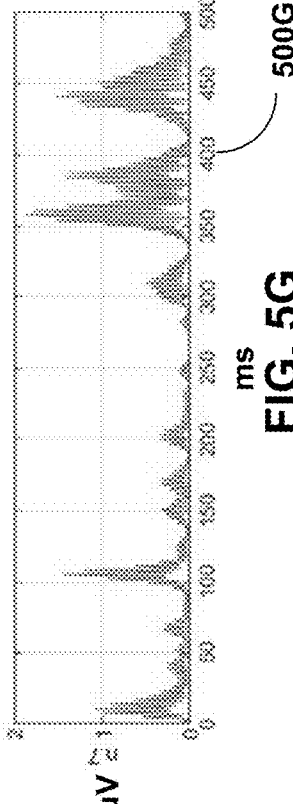
Figure 5I:
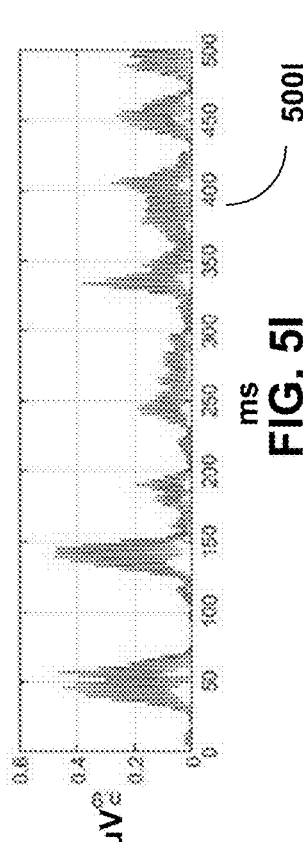
Figures 6A, 6B, 6C, 6D, 6E, 6F:
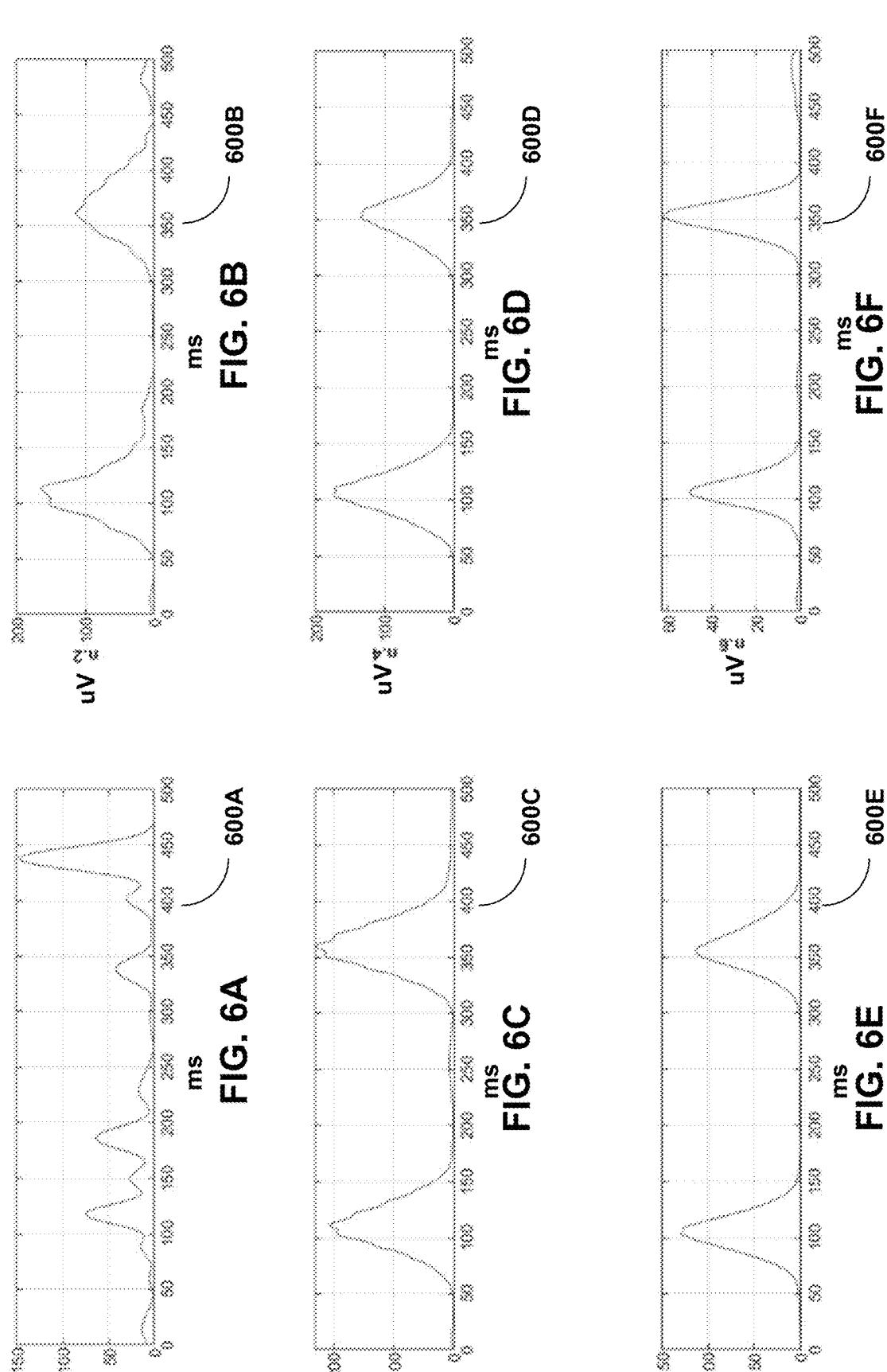
Figure 6H:
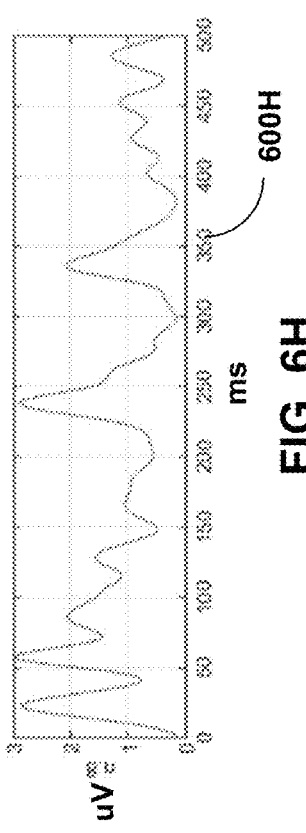
Figure 6J:
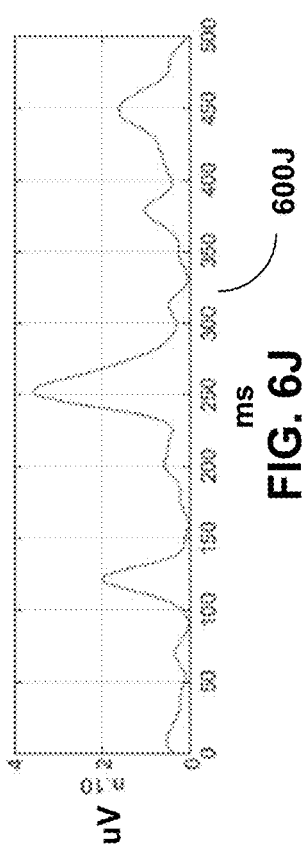
Figure 6G:
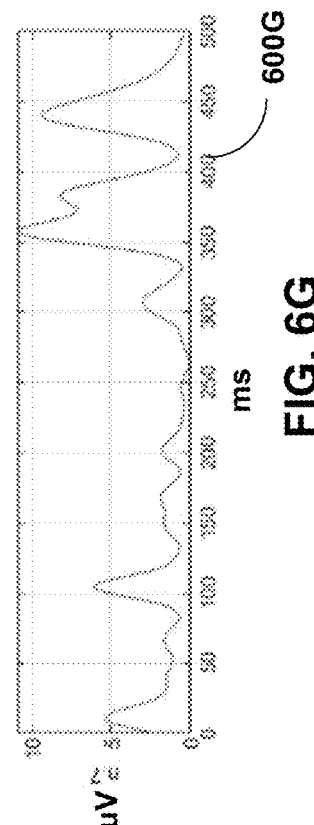
Figure 6I:
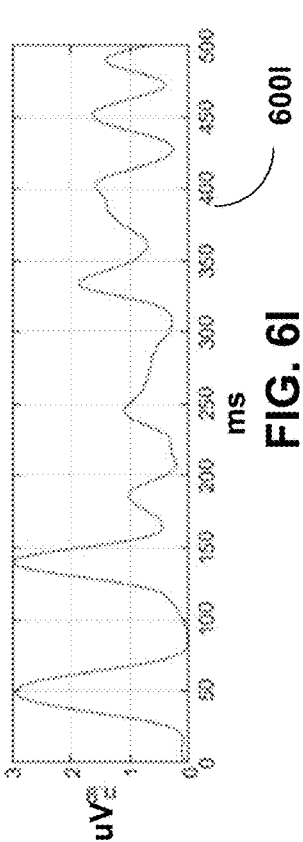

FIG. 3 is a block diagram of the external programmer of FIG. 1 for controlling delivery of DBS therapy according to an example of the techniques of the disclosure.

FIGS. 4A-4J are graphs illustrating examples of a sensed signal decomposed into a plurality of components.

FIGS. 5A-5J are graphs illustrating examples of the graphs of the plurality of components of FIGS. 4A-4J squared.

FIGS. 6A-6J are graphs illustrating examples of the graphs of FIGS. 5A-5J convolved with a triangular function.

Figure 7:
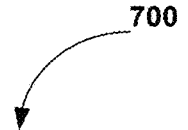
Figure 7:
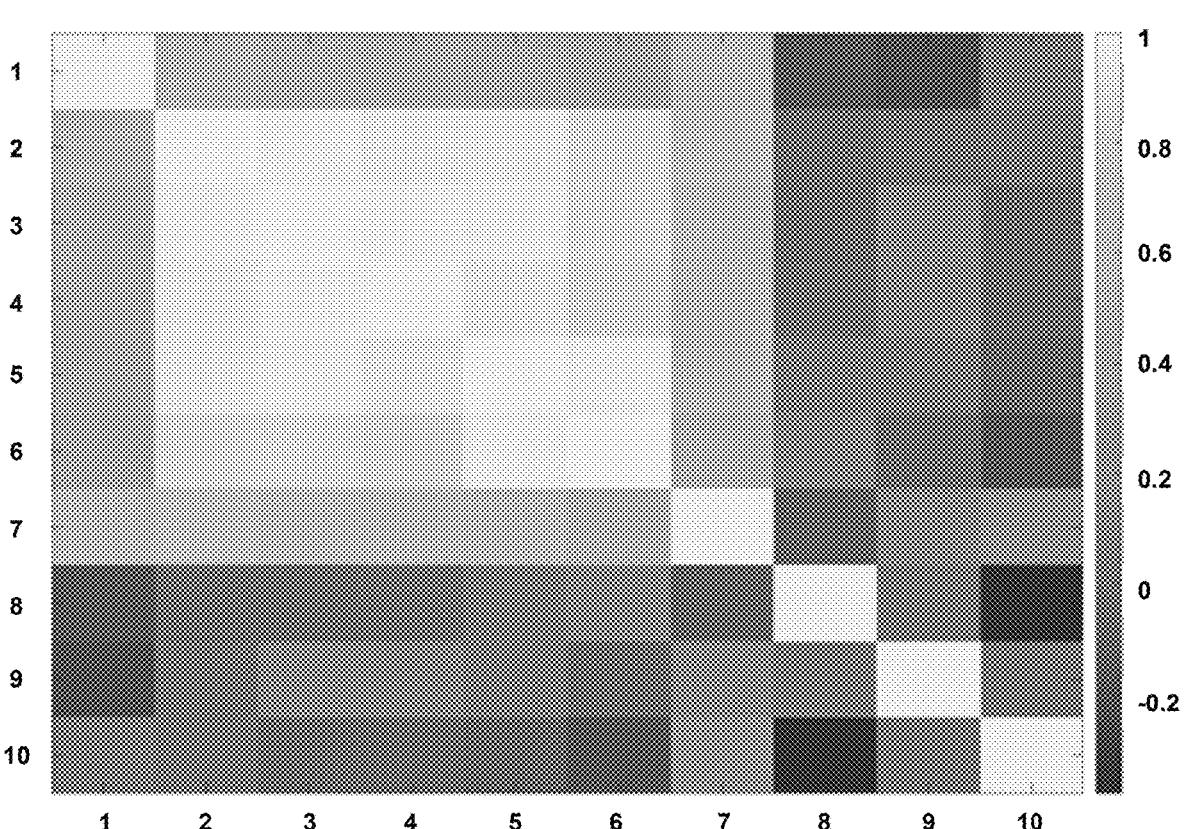

FIG. 7 is a conceptual diagram illustrating information indicative of correlation between the plurality of components that are generated by decomposing of the sensed signal.

Figure 8:
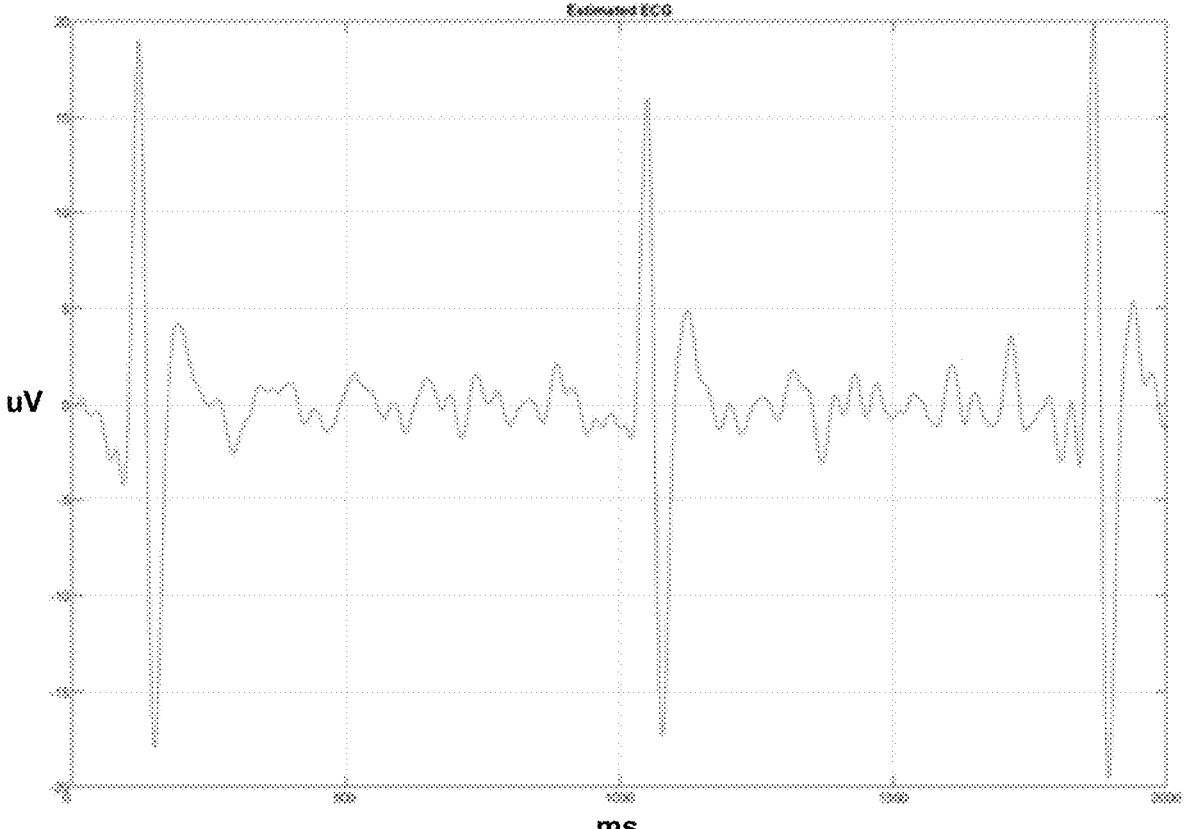

FIG. 8 is a graph illustrating an example of an estimate of a cardiac signal that is noise in the sensed signal generated based on the correlation between the plurality of components.

Figures 9A, 9B:
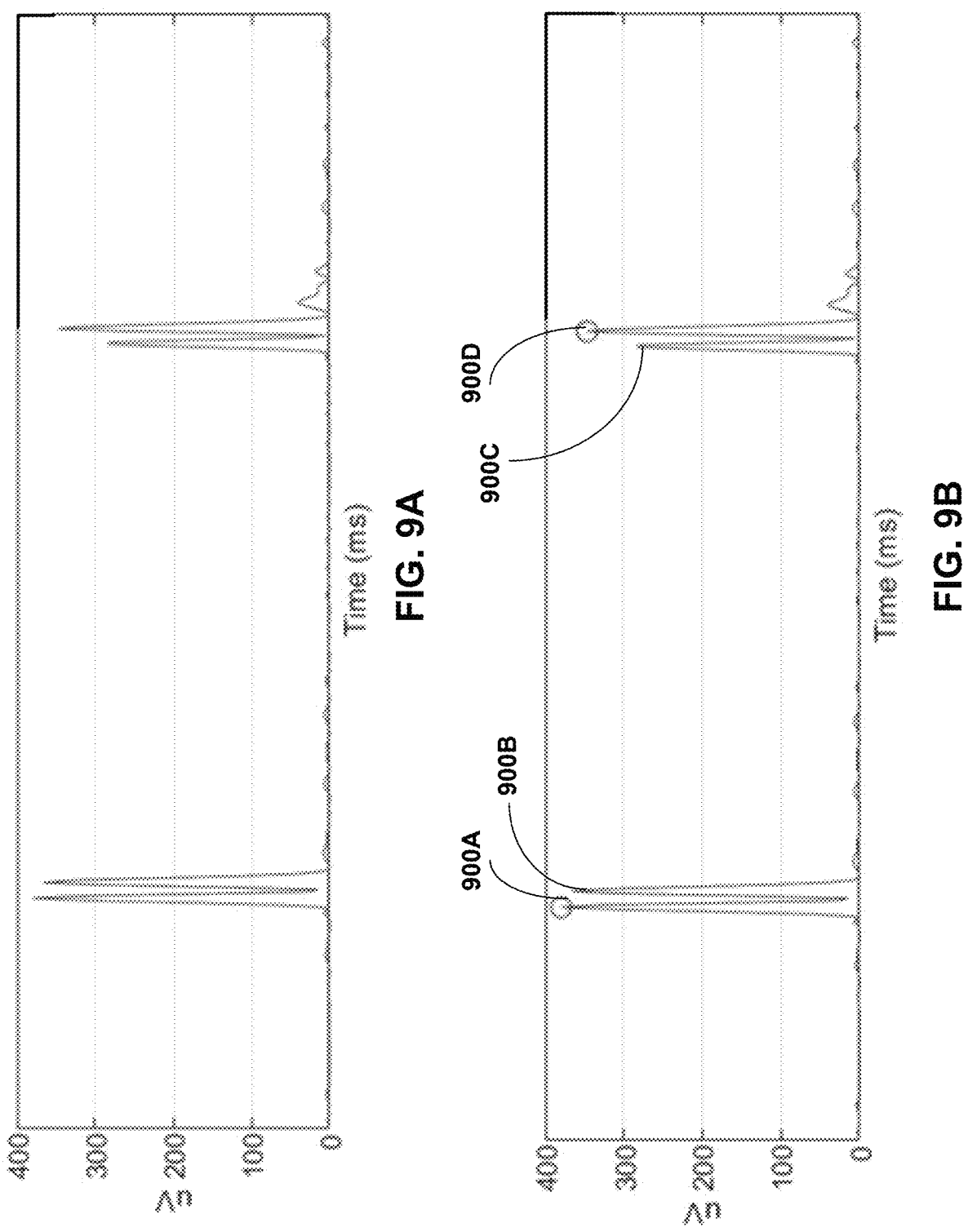

FIG. 9A is a graph illustrating the graph of FIG. 8 squared.

FIG. 9B is a graph illustrating estimated peaks of the graph of FIG. 9A.

Figure 9C:
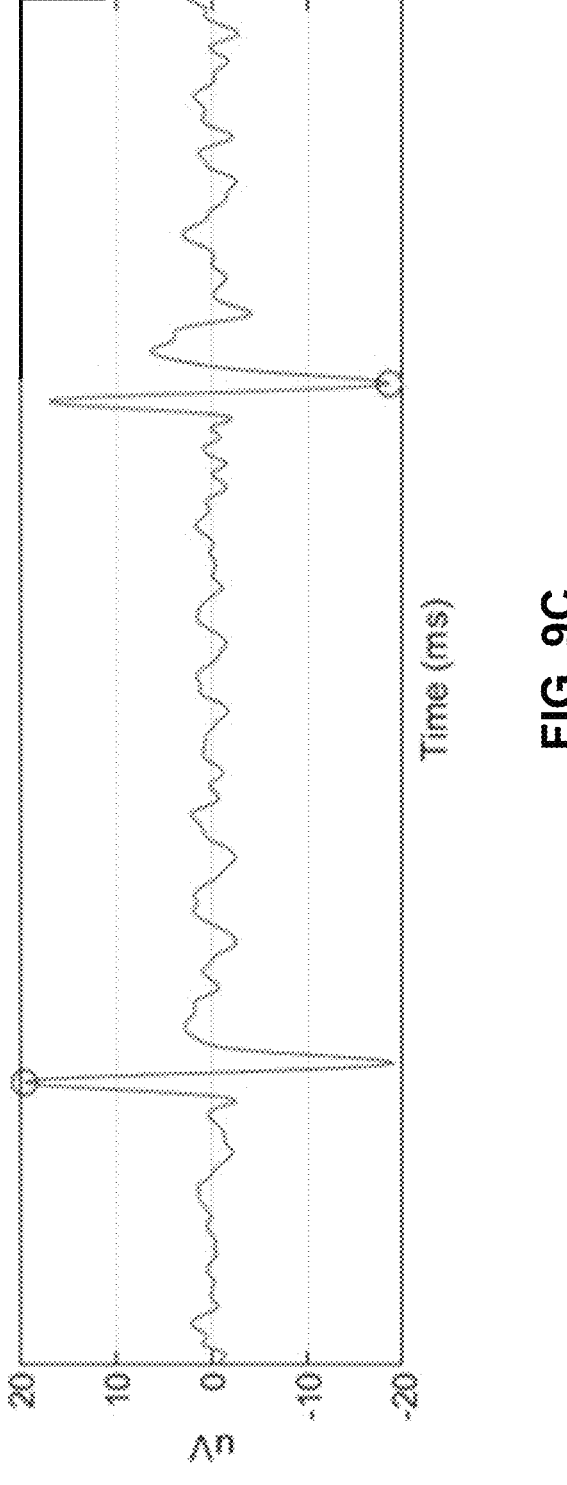

FIG. 9C is a graph illustrating the estimated peaks in the graph of FIG. 8 based on the estimated peaks in the graph of FIG. 9B.

Figure 10:
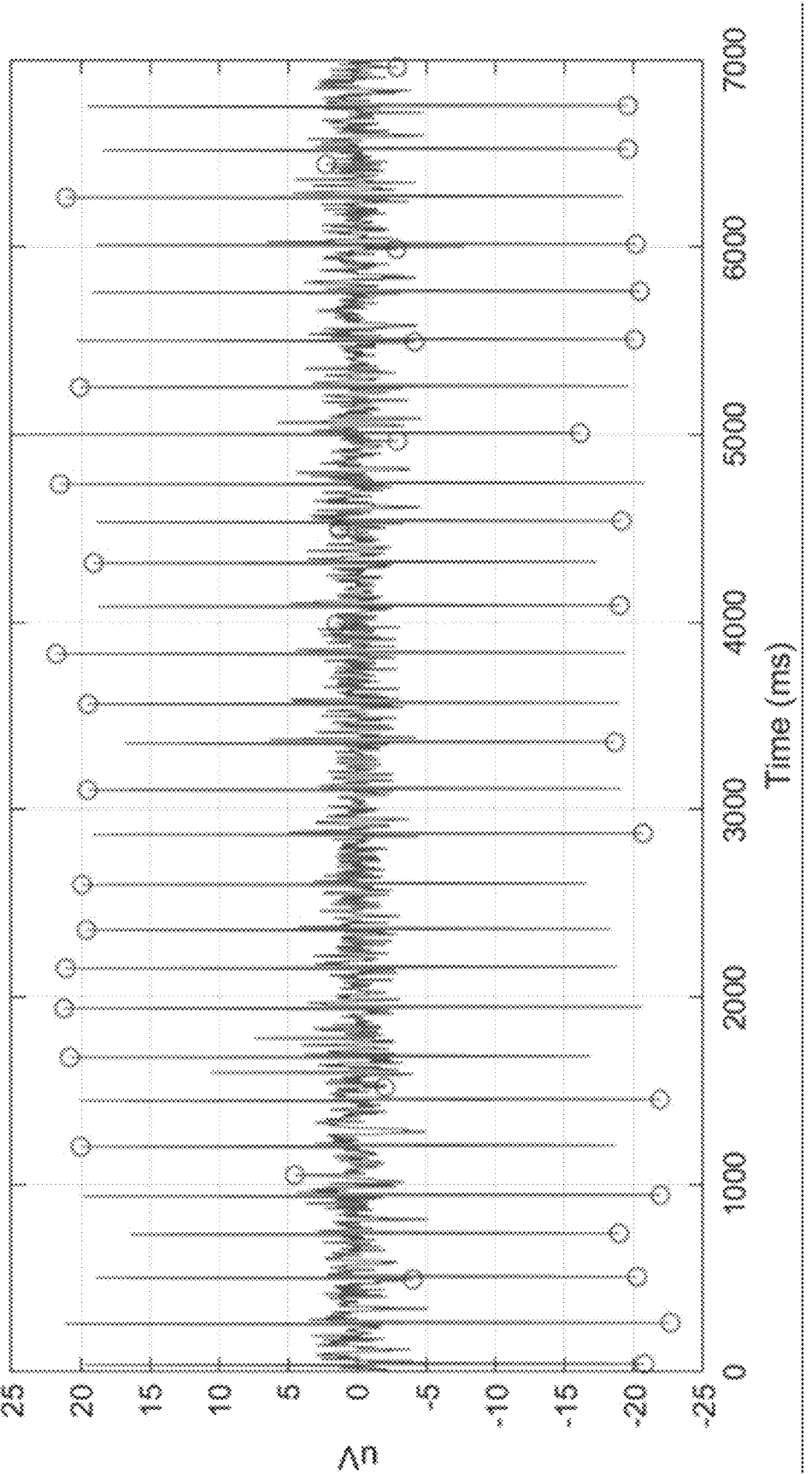

FIG. 10 is a graph illustrating a concatenation of a plurality of time windows of the estimate of the cardiac signal, including the estimate of the cardiac signal of FIG. 8 and the estimated peaks of FIG. 9C.

Figure 11:
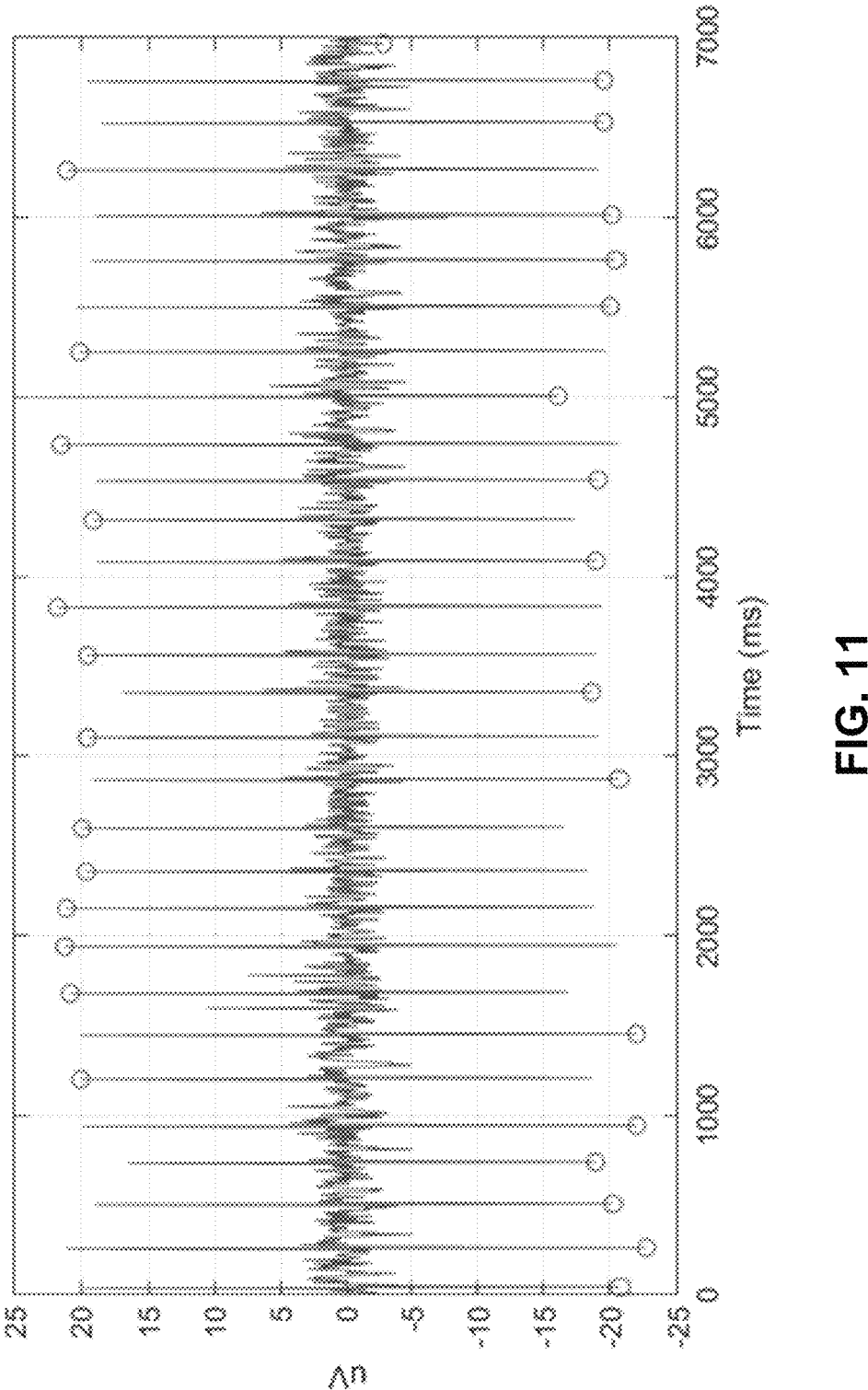

FIG. 11 is a graph illustrating the graph of FIG. 10 with removal of false positives.

Figure 12:
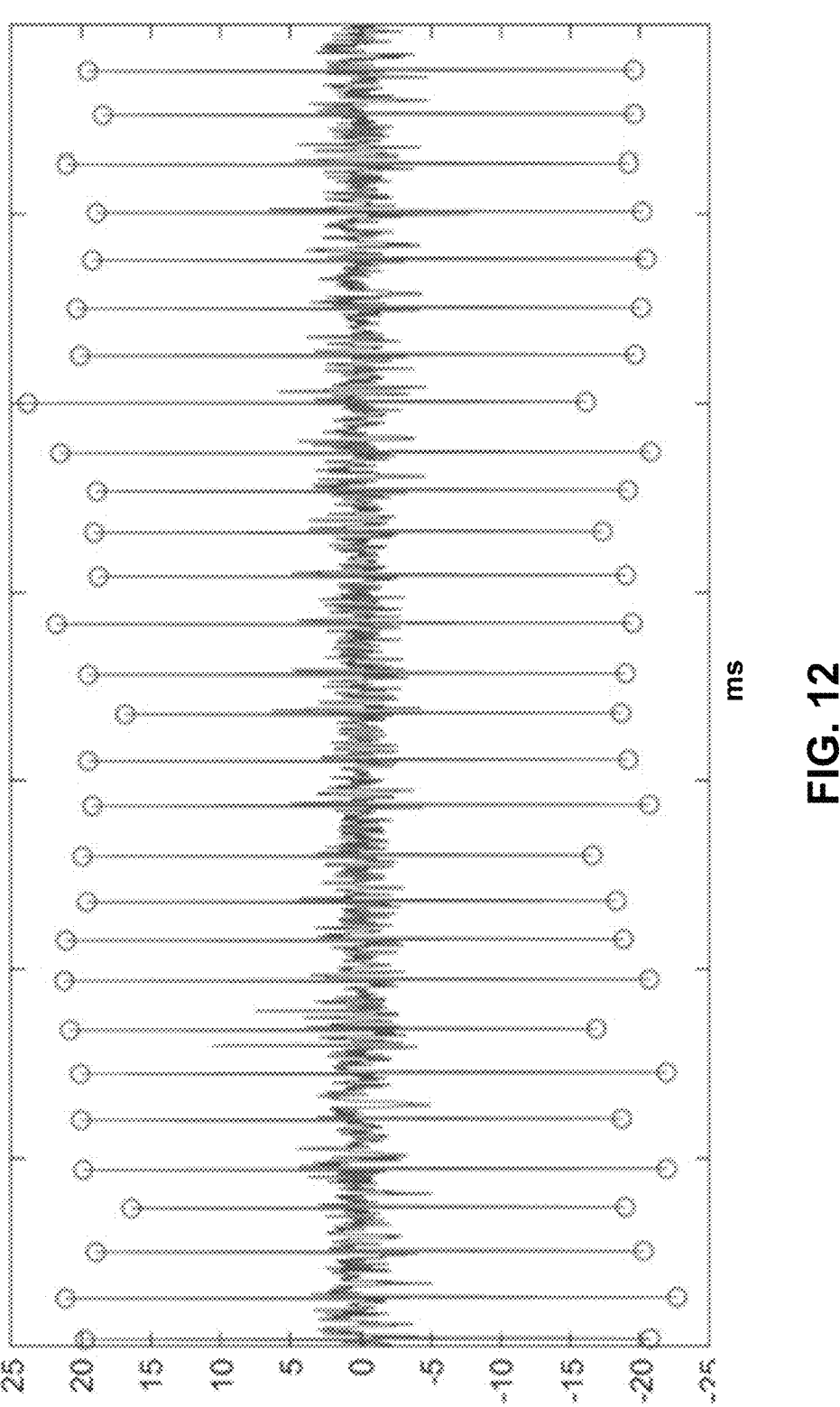

FIG. 12 is a graph illustrating example peaks for determining information of a cardiac signal.

Figure 13:

FIG. 13 is a graph illustrating an example of the R-R interval of the heart of the patient.

Figures 14A, 14B, 14C, 14D:
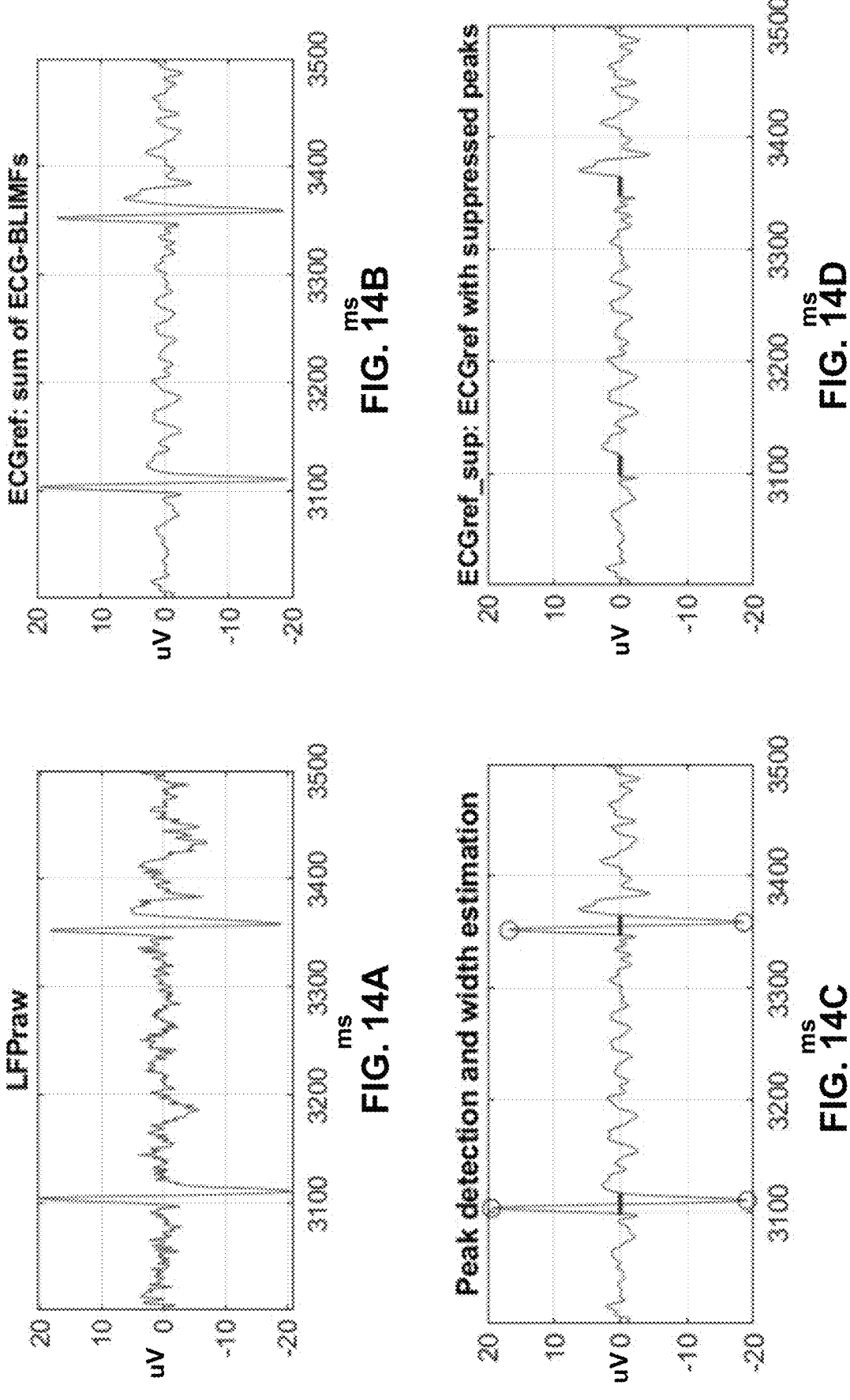

FIG. 14A is a graph illustrating an example of a sensed signal that includes artifacts from a cardiac signal that is sensed in a brain of a patient.

FIG. 14B is a graph illustrating an example of a sum of a first group of components of a plurality of components of the sensed signal that form an estimate of the cardiac signal that includes components of the neural signal.

FIG. 14C is a graph illustrating an example of peak detection and width estimation of the cardiac signal components in the estimate of the cardiac signal that includes components of the neural signal.

FIG. 14D is a graph illustrating an example of the suppression of the local peaks from the example of FIG. 14C.

Figure 14F:
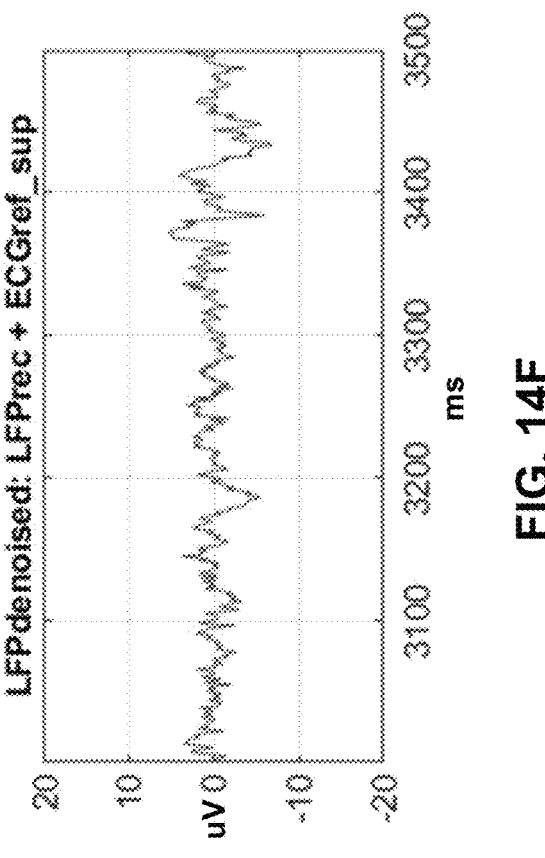
Figure 14E:
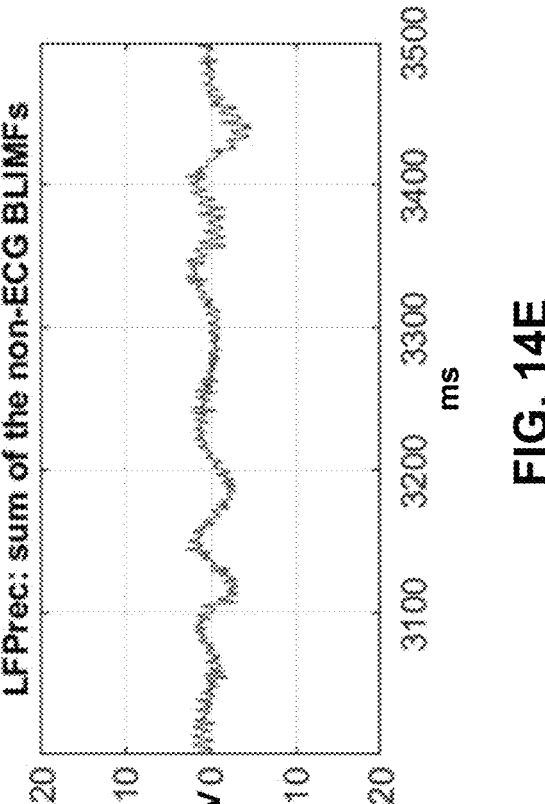

FIG. 14E is a graph illustrating an example of a sum of a second group of components of the sensed signal that excludes the first group of components.

FIG. 14F is a graph illustrating an example of the sum of the graphs of FIG. 14E and FIG. 14D showing a sensed signal having the artifacts from a cardiac signal removed.

Figure 15:
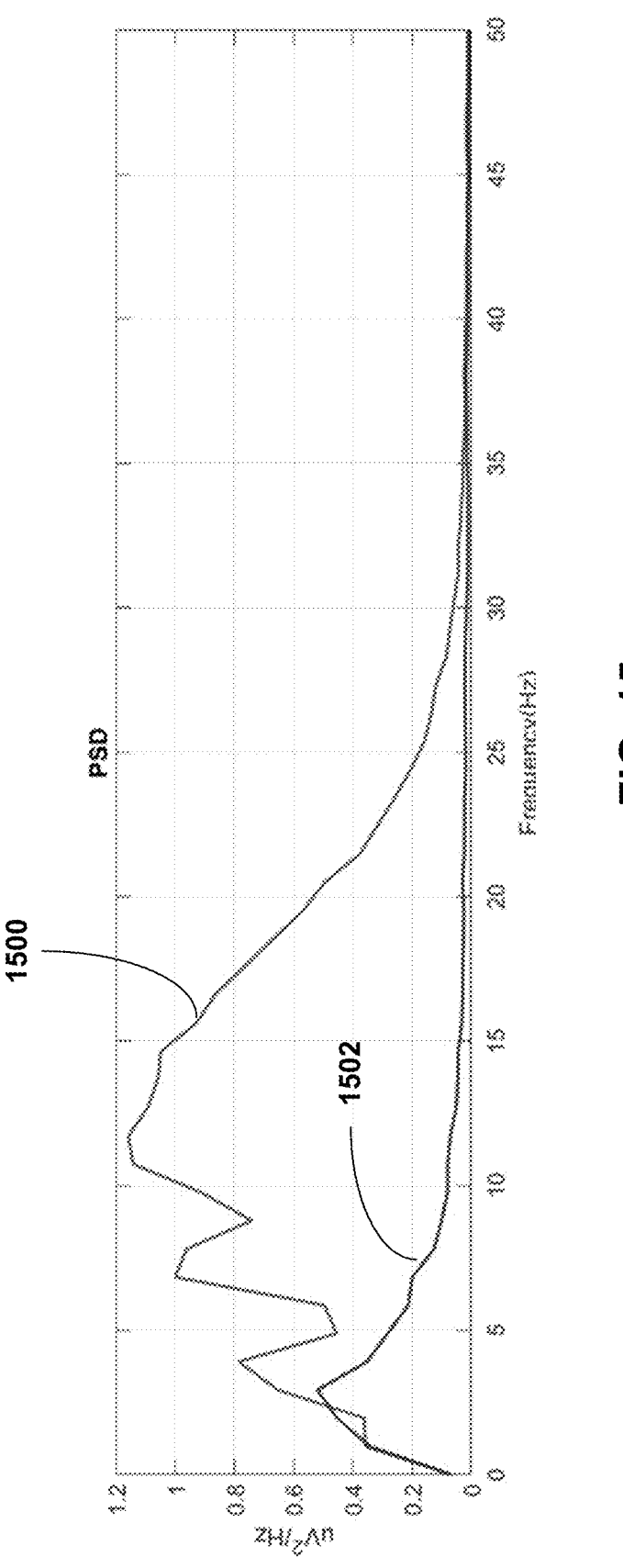

FIG. 15 is a graph illustrating a power versus frequency of a sensed signal including artifacts from a cardiac signal and a sensed signal having artifacts from the cardiac signal removed.

FIG. 16 is a flowchart illustrating an example technique according to one or more examples described in this disclosure.

DETAILED DESCRIPTION

This disclosure describes various devices, systems, and techniques for denoising sensed signals to reduce or remove artifacts from cardiac signals. A patient may suffer from one or more symptoms treatable by electrical stimulation therapy. For example, a patient may suffer from brain disorder such as Parkinson's disease or other movement disorders, Epilepsy, Alzheimer's disease, or another type of disorder. Deep brain stimulation (DBS) may be an effective treatment to reduce the symptoms associated with such disorders. However, efficacy of stimulation therapy may be reliant on selecting appropriate electrodes and other stimulation parameter values that direct an electric field to a target region of tissue. Stimulation of tissue outside of the target region or with stimulation parameters that are too high or too low may elicit undesirable effects and/or reduce the efficacy of the therapy.

In some example techniques, a medical device receives sensed electrical signals within the brain, such as local field potentials (LFPs), and based on the amplitude, frequency, or other characteristics of the sensed LFPs, the medical device may determine values of one or more therapy parameters (e.g., voltage or current amplitude, pulse width, and/or frequency). The stimulation signal that the medical device outputs may be based on the one or more therapy parameters. Rather than or in addition to the medical device, one or more other devices (e.g., programmer, computers in a cloud-computing environment, etc.) may determine values or adjustment to the values of the one or more therapy parameters, generally referred to as determining the one or more therapy parameters. In some examples, rather than or in addition to determining values of one or more therapy parameters, the medical device or some other device may utilize the sensed LFPs for assisting with diagnostic functions (e.g., output information representative of or relating to the sensed LFPs that a physician can review for purposes of diagnosis or other analytical purposes). However, there may be noise on the sensed LFPs from various sources, such as cardiac signals (e.g., electrocardiography).

As described herein, various devices, systems, and techniques may include denoising local field potential (LFP) to reduce or remove artifacts caused by cardiac signals. For ease of description, the examples are described with respect to an LFP, as a neural signal, and an electrocardiogram (ECG), as a cardiac signal. However, the example techniques are not so limited. Also, although this disclosure is directed to DBS therapy, the systems, devices, and techniques described herein may be applicable to sensing of other signals, such as sensing of signals in spinal cord stimulation (SCS), pelvic stimulation, gastric stimulation, or peripheral nerve field stimulation (PNFS). Moreover, a human patient is described for example purposes herein, but similar systems, devices, and techniques may be used for other animals in other examples.

For DBS, a lead implanted in the brain includes electrodes for sensing LFPs. A medical device receives sensed signals from the electrodes, where the sensed signals represent the LFPs. In some examples, the medical device controls values of the therapy parameters of the therapy based on the sensed signals. For instance, the medical device sets the amplitude, pulse width, and/or frequency of electrical stimulation delivered to the brain. The medical device may also determine the timing of when to deliver the electrical stimulation based on the sensed signals. The medical device may sense the LFPs for diagnostic or other analytical purposes as well.

However, electrical signals from the heart, such as electrocardiograms (ECGs) or other signals, add artifacts to the LFP signals. The magnitude of the ECG artifact is often 3 orders of magnitude larger than the sensed LFP signals and the spectral content (1-40 Hz) significantly overlaps with the LFP signals of interest (e.g., for movement disorders, 3-7 Hz theta band for dystonia and essential tremor, or 13-30 Hz beta band for Parkinson's disease). Accordingly, the medical device may not be able to determine the actual LFP from the sensed signal due to the artifacts from the ECG.

This disclosure describes example techniques to identify components in the sensed signals that represent the artifacts to suppress (e.g., remove or "zero out") so that the remaining signal represents the actual LFPs. As one example, the artifacts (e.g., ECG signal) tend to be periodic, in that the ECG signal repeats generally at set intervals. This disclosure describes example techniques to exploit the periodicity of the ECG signal and the relative high amplitude of the ECG to identify and then remove the ECG signal from the sensed signals.

In one or more examples, a medical device may receive a sensed signal that is sensed in a brain of a patient, where the sensed signal includes artifacts from a cardiac signal. The medical device may decompose the sensed signal into constituent components. Each component is a time-varying signal that includes a plurality of frequencies, such that when each component is summed together, the result is the original sensed signal. Stated another way, the medical device may decompose the sensed signal into a plurality of components, with each component having different spectral content contained in a narrow frequency band. There may be some overlap of spectral content between components but not full overlap.

The medical device may determine which of the components are highly correlated (e.g., the amplitudes of the highly correlated components increase and decrease at substantially the same time). The components that are highly correlated may be a first group of components, and the remaining components may be a second group of components.

The medical device may sum together the highly correlated components to form an estimate of the ECG signal. Because the ECG signal tends to be periodic, the highly correlated components in the sensed signal may be due to the ECG signal. Also, the estimate of the ECG signal may not necessarily mean that the estimate of the ECG signal includes only the ECG signal. Rather, the estimate of the ECG signal also includes components of the LFP signal. That is, the term "estimate of the ECG signal" or "estimate of the cardiac signal" may refer to an estimate of the cardiac signal that includes components of the neural signal.

The medical device may then determine the peaks and width of peaks in the estimate of the ECG signal. The peaks may be local peaks with relatively high amplitude, regular (e.g., periodic) distance, minimum distances between peaks, etc. Because the ECG signal tends to have relatively high and/or periodic peaks, and much higher amplitude than the LFP signal and/or regular peaks, the local peaks with relatively high amplitude and/or periodicity may be due to the ECG and not the LFP signal. The use of amplitude is optional for determining whether a local peak is due to the cardiac signal (e.g., ECG signal).

As an example, the medical device may evaluate for a maximum number of peaks in a segment of T=2 seconds. The maximum number of peaks in the short time segment is calculated based on the minimum peak distance, which is fixed. Example may be min R-R interval=min_peak_distance=600 ms, T/min_peak_distance=2000/600=3. Therefore, up to 3 local peaks will be detected which are at least 600 ms distant from each other.

In some examples, the maximum_peak_distance, or other ECG characteristics parameters may also be used to detect the peak. But in the current findpeak function offers only min_peak_distance and the Maximum number of Peak as option. The amplitude threshold is also an option, but this is not as stable as the R-R interval, varying even within the same dataset For the determined width of peaks, the medical device may suppress the estimate of the ECG signal. For instance, if there is peak that is determined to likely from the ECG signal, the medical device may set the amplitude for the time duration of the peak (e.g., the peak width) equal to zero (e.g., "zero out" the estimate of the ECG signal). The result may be the estimate of the ECG signal with suppressed peak.

The medical device may sum the estimate of the ECG signal with the suppressed peak with the second group of components (e.g., the components that were not correlated). The result may be the denoised LFP signal. The medical device may utilize the denoised LFP signal for controlling therapy and/or for outputting (e.g., for diagnostic purposes).

Moreover, in some examples, the medical device may utilize the estimate of the ECG signal to determine parameters for the heart. For instance, as described above, because the peaks of the estimate of the ECG signal may be due to the ECG signal, differences between the peaks may be indicative of the R-R interval of the ECG signal of the heart. In this way, by utilizing electrodes implanted in the brain of the patient, there may be a possibility to determine cardiac health without necessarily implanting electrodes near the heart. That is, what is noise for the LFP signal can be extracted to determine cardiac health.

FIG. 1 is a conceptual diagram illustrating an example system 100 that includes an implantable medical device (IMD) 106 configured to deliver DBS to patient 122 according to an example of the techniques of the disclosure. As shown in the example of FIG. 1, example system 100 includes medical device programmer 104, implantable medical device (IMD) 106, lead extension 110, and leads 114A and 114B with respective sets of electrodes 116, 118. In the example shown in FIG. 1, electrodes 116, 118 of leads 114A, 114B are positioned to deliver electrical stimulation to a tissue site within brain 120, such as a deep brain site under the dura matter of brain 120 of patient 112. In some examples, delivery of stimulation to one or more regions of brain 120, such as the subthalamic nucleus, globus pallidus or thalamus, may be an effective treatment to manage movement disorders, such as Parkinson's disease. Some or all of electrodes 116, 118 also may be positioned to sense neurological brain signals (e.g., neural signals such as local field potentials (LFPs)) within brain 120 of patient 112. In some examples, some of electrodes 116, 118 may be configured to sense neurological brain signals and others of electrodes 116, 118 may be configured to deliver adaptive electrical stimulation to brain 120. In other examples, all of electrodes 116, 118 are configured to both sense neurological brain signals and deliver adaptive electrical stimulation to brain 120.

IMD 106 includes a therapy module (e.g., which may include processing circuitry, signal generation circuitry or other electrical circuitry configured to perform the functions attributed to IMD 106) that includes stimulation circuitry configured to generate and deliver electrical stimulation therapy to patient 112 via a subset of electrodes 116, 118 of leads 114A and 114B, respectively. The subset of electrodes 116, 118 that are used to deliver electrical stimulation to patient 112, and, in some cases, the polarity of the subset of electrodes 116, 118, may be referred to as a stimulation electrode combination. The stimulation electrode combination can be selected for a particular patient 112 and target tissue site (e.g., selected based on the patient condition). The group of electrodes 116, 118 includes at least one electrode and can include a plurality of electrodes. In some examples, the plurality of electrodes 116 and/or 118 may have a complex electrode geometry such that two or more electrodes of the lead are located at different positions around the perimeter of the respective lead (e.g., different positions around a longitudinal axis of the lead).

In some examples, the neural signals (e.g., an example type of electrical signals) sensed within brain 120 may reflect changes in electrical current produced by the sum of electrical potential differences across brain tissue. Examples of neuro signals (also called neurological brain signals or neuro signals) include, but are not limited to, electrical signals generated from local field potentials (LFP) sensed within one or more regions of brain 120, such as an electroencephalogram (EEG) signal, or an electrocorticogram (ECoG) signal. Local field potentials, however, may include a broader genus of electrical signals within brain 120 of patient 112.

In some examples, stimulation electrode combinations may be selected based on neural signals sensed within neural tissue. The neural signals that are used to select a stimulation electrode combination may be sensed within the same region of brain 120 as the target tissue site for the electrical stimulation. These tissue sites may include tissue sites within anatomical structures such as the thalamus, subthalamic nucleus or globus pallidus of brain 120, as well as other target tissue sites. The specific target tissue sites and/or regions within brain 120 may be selected based on the patient condition. Thus, due to these differences in target locations, in some examples, the electrodes used for delivering electrical stimulation may be different than the electrodes used for sensing neurological brain signals. In other examples, the same electrodes may be used to deliver electrical stimulation and sense brain signals.

Electrical stimulation generated by IMD 106 may be configured to manage a variety of disorders and conditions. In some examples, the stimulation circuitry of IMD 106 is configured to generate and deliver electrical stimulation pulses to patient 112 via electrodes of a selected stimulation electrode combination. However, in other examples, the stimulation circuitry of IMD 106 may be configured to generate and deliver a continuous wave signal, e.g., a sine wave or triangle wave. In either case, a stimulation circuitry within IMD 106 may generate the electrical stimulation therapy for DBS according to a therapy program that is selected at that given time in therapy. In examples in which IMD 106 delivers electrical stimulation in the form of stimulation pulses, a therapy program may include a set of therapy parameter values (e.g., stimulation parameters), such as a stimulation electrode combination for delivering stimulation to patient 112, pulse frequency, pulse width, and a current or voltage amplitude of the pulses. As previously indicated, the electrode combination may indicate the specific electrodes 116, 118 that are selected to deliver stimulation signals to tissue of patient 112 and the respective polarities of the selected electrodes. IMD 106 may deliver electrical stimulation intended to contribute to a therapeutic effect. In some examples, IMD 106 may also, or alternatively, deliver electrical stimulation intended to be sensed by one or more other electrodes and/or elicit a physiological response, such as an evoked compound action potential (ECAP), that can be sensed by electrodes.

In some examples, the therapy parameter values may be set based on the sensed signals. For instance, based on the amplitude of the neural signal, IMD 106 may select a higher or lower amplitude for the electrical stimulation. IMD 106 may similarly determine pulse width and frequency. In one or more examples, IMD 106 may determine the duration and timing of when to deliver electrical stimulation based on the sensed signals. For instance, IMD 106 may determine to deliver stimulation when the amplitude of the neural signal is greater than a threshold, as amplitudes of neural signals above the threshold may indicate onset or occurrence of an event for which therapy is desired.

IMD 106 may be implanted within a subcutaneous pocket above the clavicle, or, alternatively, on or within cranium 122 or at any other suitable site within patient 112. Generally, IMD 106 is constructed of a biocompatible material that resists corrosion and degradation from bodily fluids. IMD 106 may comprise a hermetic housing to substantially enclose components, such as a processor, therapy module, and memory.

As shown in FIG. 1, implanted lead extension 110 is coupled to IMD 106 via connector 108 (also referred to as a connector block or a header of IMD 106). In the example of FIG. 1, lead extension 110 traverses from the implant site of IMD 106 and along the neck of patient 112 to cranium 122 of patient 112 to access brain 120. In the example shown in FIG. 1, leads 114A and 114B (collectively "leads 114") are implanted within the right and left hemispheres, respectively, of patient 112 in order deliver electrical stimulation to one or more regions of brain 120, which may be selected based on the patient condition or disorder controlled by therapy system 100. The specific target tissue site and the stimulation electrodes used to deliver stimulation to the target tissue site, however, may be selected, e.g., according to identified patient behaviors and/or other sensed patient parameters. Other implant sites for lead 114 and IMD 106 are contemplated. For example, IMD 106 may be implanted on or within cranium 122, in some examples. Leads 114 may be implanted within the same hemisphere or IMD 106 may be coupled to a single lead implanted in a single hemisphere. Although leads 114 may have ring electrodes at different longitudinal positions as shown in FIG. 1, leads 114 may have electrodes disposed at different positions around the perimeter of the lead (e.g., different circumferential positions for a cylindrical shaped lead).

Leads 114 illustrate an example lead set that includes axial leads carrying ring electrodes disposed at different axial positions (or longitudinal positions). In other examples, leads may be referred to as "paddle" leads carrying planar arrays of electrodes on one side of the lead structure. In addition, complex lead array geometries may be used in which electrodes are disposed at different respective longitudinal positions and different positions around the perimeter of the lead.

Although leads 114 are shown in FIG. 1 as being coupled to a common lead extension 110, in other examples, leads 114 may be coupled to IMD 106 via separate lead extensions or directly to connector 108. Leads 114 may be positioned to deliver electrical stimulation to one or more target tissue sites within brain 120 to manage patient symptoms associated with a movement disorder of patient 112. Leads 114 may be implanted to position electrodes 116, 118 at desired locations of brain 120 through respective holes in cranium 122. Leads 114 may be placed at any location within brain 120 such that electrodes 116, 118 are capable of providing electrical stimulation to target tissue sites within brain 120 during treatment. For example, electrodes 116, 118 may be surgically implanted under the dura mater of brain 120 or within the cerebral cortex of brain 120 via a burr hole in cranium 122 of patient 112, and electrically coupled to IMD 106 via one or more leads 114.

In the example shown in FIG. 1, electrodes 116, 118 of leads 114 are shown as ring electrodes. Ring electrodes may be used in DBS applications because they are relatively simple to program and are capable of delivering an electrical field to any tissue adjacent to electrodes 116, 118. In other examples, electrodes 116, 118 may have different configurations. For example, in some examples, at least some of the electrodes 116, 118 of leads 114 may have a complex electrode array geometry that is capable of producing shaped electrical fields. The complex electrode array geometry may include multiple electrodes (e.g., partial ring or segmented electrodes) around the outer perimeter of each lead 114, rather than one ring electrode. In this manner, electrical stimulation may be directed in a specific direction from leads 114 to enhance therapy efficacy and reduce possible adverse side effects from stimulating a large volume of tissue. In some examples, a housing of IMD 106 may include one or more stimulation and/or sensing electrodes. In alternative examples, leads 114 may have shapes other than elongated cylinders as shown in FIG. 1. For example, leads 114 may be paddle leads, spherical leads, bendable leads, or any other type of shape effective in treating patient 112 and/or minimizing invasiveness of leads 114.

In the example shown in FIG. 1, IMD 106 includes a memory to store a plurality of therapy programs that each define a set of therapy parameter values. In some examples, IMD 106 may select a therapy program from the memory based on various parameters, such as sensed patient parameters and the identified patient behaviors. IMD 106 may generate electrical stimulation based on the selected therapy program to manage the patient symptoms associated with a movement disorder.

External programmer 104 wirelessly communicates with IMD 106 as needed to provide or retrieve therapy information. Programmer 104 is an external computing device that the user, e.g., a clinician and/or patient 112, may use to communicate with IMD 106. For example, programmer 104 may be a clinician programmer that the clinician uses to communicate with IMD 106 and program one or more therapy programs for IMD 106. Alternatively, programmer 104 may be a patient programmer that allows patient 112 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 106.

When programmer 104 is configured for use by the clinician, programmer 104 may be used to transmit initial programming information to IMD 106. This initial information may include hardware information, such as the type of leads 114 and the electrode arrangement, the position of leads 114 within brain 120, the configuration of electrode array 116, 118, initial programs defining therapy parameter values, and any other information the clinician desires to program into IMD 106. Programmer 104 may also be capable of directing IMD 106 to complete functional tests (e.g., measuring the impedance of electrodes 116, 118 of leads 114). In some examples, programmer 104 may receive sensed signals or representative information and perform the same techniques and functions attributed to IMD 106 herein.

In other examples, a remote server (e.g., a standalone server or part of a cloud service) may perform the functions attributed to IMD 106, programmer 104, or any other devices described herein.

The clinician may also store therapy programs within IMD 106 with the aid of programmer 104. During a programming session, the clinician may determine one or more therapy programs that may provide efficacious therapy to patient 112 to address symptoms associated with the patient condition, and, in some cases, specific to one or more different patient states, such as a sleep state, movement state or rest state. For example, the clinician may select one or more stimulation electrode combinations with which stimulation is delivered to brain 120. During the programming session, the clinician may evaluate the efficacy of the specific program being evaluated based on feedback provided by patient 112 or based on one or more physiological parameters of patient 112 (e.g., muscle activity, muscle tone, rigidity, tremor, etc.). Alternatively, identified patient behavior from video information may be used as feedback during the initial and subsequent programming sessions. Programmer 104 may assist the clinician in the creation/identification of therapy programs by providing a methodical system for identifying potentially beneficial therapy parameter values.

Programmer 104 may also be configured for use by patient 112. When configured as a patient programmer, programmer 104 may have limited functionality (compared to a clinician programmer) in order to prevent patient 112 from altering critical functions of IMD 106 or applications that may be detrimental to patient 112. In this manner, programmer 104 may only allow patient 112 to adjust values for certain therapy parameters or set an available range of values for a particular therapy parameter.

Programmer 104 may also provide an indication to patient 112 when therapy is being delivered, when patient input has triggered a change in therapy or when the power source within programmer 104 or IMD 106 needs to be replaced or recharged. For example, programmer 112 may include an alert LED, may flash a message to patient 112 via a programmer display, generate an audible sound or somatosensory cue to confirm patient input was received, e.g., to indicate a patient state or to manually modify a therapy parameter.

Therapy system 100 may be implemented to provide chronic stimulation therapy to patient 112 over the course of several months or years. However, system 100 may also be employed on a trial basis to evaluate therapy before committing to full implantation. If implemented temporarily, some components of system 100 may not be implanted within patient 112. For example, patient 112 may be fitted with an external medical device, such as a trial stimulator, rather than IMD 106. The external medical device may be coupled to percutaneous leads or to implanted leads via a percutaneous extension. If the trial stimulator indicates DBS system 100 provides effective treatment to patient 112, the clinician may implant a chronic stimulator within patient 112 for relatively long-term treatment.

Although IMD 106 is described as delivering electrical stimulation therapy to brain 120, IMD 106 may be configured to direct electrical stimulation to other anatomical regions of patient 112 in other examples. In other examples, system 100 may include an implantable drug pump in addition to, or in place of, IMD 106. Further, an IMD may provide other electrical stimulation such as spinal cord stimulation to treat a movement disorder.

In some cases, cardiac signals, such as electrocardiography (ECG) or other signals, add artifacts to the neural (e.g., LFP) signals. The magnitude of the ECG artifact is often 3 orders of magnitude larger than the sensed LFP signals and the spectral content (1-40 Hz) significantly overlaps with the LFP signals of interest (e.g., for movement disorders, 3-7 Hz theta band for dystonia and essential tremor, or 13-30 Hz beta band for Parkinson's disease). Accordingly, IMD 106 may not be able to determine the actual LFP from the sensed signal due to the artifacts from the ECG.

This disclosure describes example techniques to identify components in the sensed signals that represent the artifacts to remove the artifacts (e.g., a cardiac signal) from the sensed signal, or reduce the artifacts, such that the remaining signal represents the actual LFPs (e.g., a neural signal) with no artifacts or reduced artifacts. For instance, IMD 106 may receive a sensed signal that is sensed in brain 120 of patient 122, where the sensed signal includes a neural signal and artifacts from a cardiac signal.

IMD 106 may decompose the sensed signal into a plurality of components, each component having a plurality of frequencies. For example, each component is a time-varying signal that includes a plurality of frequencies, such that when each component is summed together, the result is the original sensed signal. Stated another way, IMD 106 may decompose the sensed signal into a plurality of components, with each component having different spectral content contained in a narrow frequency band. There may be some overlap of spectral content between components but not full overlap.

For example, IMD 106 may be configured to perform a variational mode decomposition (VIVID). In VMD, IMD 106 may decompose a series X (e.g., the sensed signal) into a discrete number of k quasi-orthogonal sub-signals (e.g., decompose the sensed signal into a plurality of components), represented as $u_k$. As an example, if the sensed signal is decomposed into ten components (e.g., k=10), each component may be represented as $u_1$, $u_2$, $u_3$, and so forth. Each of the $u_k$ signal components may be centered around a center frequency $W_k$ with a limited bandwidth. Each of the $u_k$ signal components may be referred to as a band limited intrinsic mode function (BLIMF). That is, in this example, there may be ten BLIMFs because k=10.

IMD 106 may determine a first group of components, from the plurality of components, that are correlated with one another. The first group of components include two or more components. For example, to determine the first group of components, IMD 106 may determine components of the sensed signal having amplitudes that increase or decrease at substantially the same time (e.g., within less than 1 second). That is, IMD 106 may determine which of the components are highly correlated (e.g., the amplitudes of the highly correlated components increase and decrease at substantially the same time). The components that are highly correlated may be a first group of components, and the remaining components may be a second group of components.

In general, components of a neural signal, where each component of the neural signal represents a time-varying neural signal over a limited bandwidth, tend not be correlated because the neural signal tends to not be periodic. However, components of a cardiac signal, where each component of the cardiac signal represents a time-varying cardiac signal over a limited bandwidth, tends to be correlated because the cardiac signal tends to be periodic (e.g., due to the periodic nature of a heart beat).

Therefore, the components of the sensed signal that are correlated may be correlated due to the inclusion of the cardiac signal, which is an artifact in the sensed signal. The components of the sensed signal that are correlated (e.g., the first group of components of the sensed signal) include both components of the cardiac signal and components of the neural signal. However, components of the sensed signal that are not correlated (e.g., the second group of components of the sensed signal) include components of the neural signal, but may not include components of the cardiac signal, or generally exclude the components of the cardiac signal.

As described above, each component of the sensed signal may be referred to as a BLIMF (band-limited intrinsic mode function). For instance, assume that BLIMF1, BLIMF2, BLIMF3, and BLIMF4 are each components of the sensed signal and represent time-varying sensed signals over different frequency bands, but there may be some overlap of the frequency bands. Assume that BLIMF1 and BLIMF2 are correlated, but BLIMF3 and BLIMF4 are not correlated with any of the other BLIMFs. In this example, BLIMF1 and BLIMF2 would form the first group of components, and BLIMF3 and BLIMF4 would form the second group of components. In this example, BLIMF1 and BLIMF2 include components from the cardiac signal (e.g., as artifacts) and the neural signal. BLIMF3 and BLIMF4 include components from the neural signal, but may not include components from the cardiac signal.

There may be various ways in which IMD 106 may determine the first group of components (e.g., the components of the sensed signal that are correlated with one another). As one example, IMD 106 may determine sets of adjacent components in the plurality of components. Each set of adjacent components includes sequential frequency bands. For instance, assume that BLIMF1 (e.g., a first component of the sensed signal) includes a frequency band from a first frequency to a second frequency, centered at a frequency between the first frequency and the second frequency. Assume that BLIMF2 (e.g., a second component of the sensed signal) includes frequency band from a third frequency to a fourth frequency, centered at a frequency between the third frequency and the fourth frequency. In some examples, the third frequency and the fourth frequency may be different than the first frequency and the second frequency. In some examples, the upper bound of first frequency and the second frequency, may be the same as the lower bound of the third frequency and fourth frequency (e.g., second frequency and third frequency are same).

If there is no other component having a frequency band within BLIMF1 and BLIMF2, then BLIMF1 and BLIMF2 are adjacent components. If there is a component having a frequency band within BLIMF1 and BLIMF2, then BLIMF1 and BLIMF2 are not adjacent components. For instance, assume that there are BLIMF1 and BLIMF10, where the frequency band of BLIMFN immediately follows the frequency band of BLIMF(N−1), then BLIMF1 and BLIMF2 may be considered as adjacent components, BLIMF2 and BLIMF3 may be considered as adjacent components, and so forth.

IMD 106 may determine a set of adjacent components from the set of adjacent components having a maximum correlation. For example, assume that the correlation between BLIMF3 and BLIMF4 is greater than the correlation between any other set of adjacent components. In this example, IMD 106 may include the set of adjacent components having the maximum correlation in the first group of components (e.g., include BLIMF3 and BLIMF4).

To include additional components in the first group of components, IMD 106 may determine other components that correlate with the set of adjacent components having the maximum correlation. For instance, the set of adjacent components having the maximum correlation includes a first component (e.g., BLIMF3) and a second component (e.g., BLIMF4). Assume a correlation value indicative of the correlation of the first component and the second component is maximum_correlation. IMD 106 may determine components in the plurality of components that correlate to at least one of the first component or the second component by a threshold value determined relative to the maximum correlation.

For instance, IMD 106 may determine components of the plurality of components that correlate to the first component or the second component having a correlation value that is within a minimum threshold relative to the maximum correlation. As an example, assume that maximum_correlation is equal 0.8, and a correlation threshold is 50%. In this example, IMD 106 may determine components having a correlation that is greater than 0.4 (e.g., 0.8*50%). IMD 106 may include such determined components in the first group of components.

IMD 106 may be configured to determine an estimate of the cardiac signal based on the first group of components. For instance, IMD 106 may sum together the highly correlated components (e.g., first group of components) to form an estimate of the cardiac (e.g., ECG) signal. As described, because the ECG signal tends to be periodic, the highly correlated components in the sensed signal may be due to the ECG signal. Also, the estimate of the ECG signal may not necessarily mean that the estimate of the ECG signal includes only the ECG signal. Rather, the estimate of the ECG signal also includes components of the LFP signal. For instance, assume that the estimate of the ECG signal is the summation of BLIMF1 and BLIMF2. In this example, because BLIMF1 and BLIMF2 included both components of the cardiac signal and components of the neural signal, the estimate of the cardiac signal (e.g., sum of BLIMF1 and BLIMF2) includes both the cardiac signal and the components of the neural signal.

The estimate of the cardiac signal may be referred to as "the estimate of the cardiac signal" even though the estimate of the cardiac signal includes the cardiac signal and components of the neural signal because the cardiac signal may be a predominant part of the estimate of the cardiac signal. For instance, because the amplitude of the cardiac signal may be substantially larger than the amplitude of the neural signal, the cardiac signal may be a much larger part in the estimate of the cardiac signal as compared to the components of the neural signal in the estimate of the cardiac signal.

IMD 106 may generate a denoised neural signal based on the estimated cardiac signal and a second group of components of the plurality of components of the sensed signal. The cardiac signal is suppressed in the denoised neural signal, and, as noted above, the second group of components excludes the first group of components.

For example, IMD 106 may determine the peaks and width of peaks in the estimate of the cardiac signal. The peaks may be local peaks that are relatively periodic. Because the ECG signal tends to be relatively periodic, the local peaks with relatively high periodicity may be due to the ECG and not the LFP signal.

For the determined width of peaks, IMD 106 may "zero out" the estimate of the cardiac signal. For instance, if there is a peak that is determined to likely be from the ECG signal, IMD 106 may set the amplitude for the time duration of the peak (e.g., the peak width) equal to zero. The result may be the estimate of the ECG signal with suppressed peak.

IMD 106 may sum the estimate of the ECG signal with suppressed peak with the second group of components (e.g., the components that were not correlated). The result may be the denoised LFP signal. IMD 106 may utilize the denoised LFP signal for controlling therapy or diagnostic purposes.

The above examples are described with respect to IMD 106 performing the operations. However, the techniques are not so limited. In some examples, external programmer 104 may be configured to perform the example techniques based on sensed signals that IMD 106 transmits to programmer 104. In some examples, a combination of IMD 106 and programmer 104 may be configured to perform the example techniques. Accordingly, processing circuitry may be configured to perform the example techniques described in this disclosure, and an example of the processing circuitry includes processing circuitry of IMD 106, processing circuitry of programmer 104, and/or processing circuitry of a combination of IMD 106 and programmer 104.

The architecture of system 100 illustrated in FIG. 1 is shown as an example. The techniques as set forth in this disclosure may be implemented in the example system 100 of FIG. 1, as well as other types of systems not described specifically herein.

FIG. 2 is a block diagram of the example IMD 106 of FIG. 1 for delivering DBS therapy. In the example shown in FIG. 2, IMD 106 includes processor 210, memory 211, stimulation circuitry 202, sensing circuitry 204, telemetry circuitry 208, sensor 212, and power source 220. Each of these may include electrical circuitry configured to perform the functions attributed to each respective module. For example, processor 210 may include processing circuitry. Memory 211 may include any volatile or non-volatile media, such as a random-access memory (RAM), read only memory (ROM), non-volatile RAM (NVRAM), ferroelectric RAM (FRAM), electrically erasable programmable ROM (EEPROM), flash memory, and the like. Memory 211 may store computer-readable instructions that, when executed by processor 210, cause IMD 106 to perform various functions. Memory 211 may be a storage device or other non-transitory medium.

In the example shown in FIG. 2, memory 211 stores therapy programs 214 that include respective stimulation parameter sets that define therapy. Each stored therapy program 214 defines a particular set of electrical stimulation parameters (e.g., a therapy parameter set), such as a stimulation electrode combination, electrode polarities, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

In some examples, the sense and stimulation electrode combinations may include the same subset of electrodes 116, 118, a housing of IMD 106 functioning as an electrode, or may include different subsets or combinations of such electrodes. Thus, memory 211 can store a plurality of sense electrode combinations and, for each sense electrode combination, store information identifying the stimulation electrode combination that is associated with the respective sense electrode combination. The associations between sense and stimulation electrode combinations can be determined, e.g., by a clinician or automatically by processor 210. In some examples, corresponding sense and stimulation electrode combinations may comprise some or all of the same electrodes. In other examples, however, some or all of the electrodes in corresponding sense and stimulation electrode combinations may be different. For example, a stimulation electrode combination may include more electrodes than the corresponding sense electrode combination in order to increase the efficacy of the stimulation therapy. In some examples, as discussed above, stimulation may be delivered via a stimulation electrode combination to a tissue site that is different than the tissue site closest to the corresponding sense electrode combination but is within the same region, e.g., the thalamus, of brain 120 in order to mitigate any irregular oscillations or other irregular brain activity within the tissue site associated with the sense electrode combination. In other examples, the electrodes that deliver stimulation may be carried by a lead implanted in a different region of the brain than a different lead that carries the sensing electrodes.

Stimulation circuitry 202, under the control of processor 210, generates stimulation signals for delivery to patient 112 via selected combinations of electrodes 116, 118. An example range of electrical stimulation parameters believed to be effective in DB S to manage a movement disorder of patient include:

1. Pulse Rate, i.e., Frequency: between approximately 0.1 Hertz and approximately 500 Hertz, such as between approximately 0.1 to 10 Hertz, or between approximately 40 to 185 Hertz, or such as approximately 140 Hertz.
2. In the case of a voltage controlled system, Voltage Amplitude: between approximately 0.1 volts and approximately 50 volts, such as between approximately 2 volts and approximately 3 volts.
3. In the alternative case of a current controlled system, Current Amplitude: between approximately 0.2 milliamps to approximately 100 milliamps, such as between approximately 1.3 milliamps and approximately 2.0 milliamps.
4. Pulse Width: between approximately 10 microseconds and approximately 5000 microseconds, such as between approximately 100 microseconds and approximately 1000 microseconds, or between approximately 180 microseconds and approximately 450 microseconds.

Accordingly, in some examples, stimulation circuitry 202 generates electrical stimulation signals in accordance with the electrical stimulation parameters noted above. Other ranges of therapy parameter values may also be useful, and may depend on the target stimulation site within patient 112. While stimulation pulses are described, stimulation signals may be of any form, such as continuous-time signals (e.g., sine waves) or the like. Stimulation signals configured to elicit ECAPs or other evoked physiological signals may be similar to or different from the above parameter value ranges.

Processor 210 may include fixed function processing circuitry and/or programmable processing circuitry, and may comprise, for example, any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processor 210 herein, and may be embodied as firmware, hardware, software or any combination thereof. Processor 210 may control stimulation circuitry 202 according to therapy programs 214 stored in memory 211 to apply particular stimulation parameter values specified by one or more of programs, such as voltage amplitude or current amplitude, pulse width, or pulse rate, to one or more of electrodes 116, 118. In the example shown in FIG. 2, the set of electrodes 116 includes electrodes 116A, 116B, 116C, and 116D, and the set of electrodes 118 includes electrodes 118A, 118B, 118C, and 118D.

Stimulation circuitry 202 may be a single channel or multi-channel stimulation circuitry. In particular, stimulation circuitry 202 may be capable of delivering a single stimulation pulse, multiple stimulation pulses, or a continuous signal at a given time via a single electrode combination or multiple stimulation pulses at a given time via multiple electrode combinations. In some examples, however, stimulation circuitry 202 may be configured to deliver multiple channels on a time-interleaved basis. For example, stimulation circuitry 202 may comprise multiple voltage or current sources and sinks that are coupled to respective electrodes to selectively drive the electrodes as cathodes or anodes.

Electrodes 116, 118 on respective leads 114 may be constructed of a variety of different designs. For example, one or both of leads 114 may include two or more electrodes at each longitudinal location along the length of the lead, such as multiple electrodes at different perimeter locations around the perimeter of the lead at each of the locations A, B, C, and D. As one example, the electrodes may be electrically coupled via respective wires that are straight or coiled within the housing the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 114. These and other constructions may be used to create a lead with a complex electrode geometry.

Although sensing circuitry 204 is incorporated into a common housing with stimulation circuitry 202 and processor 210 in FIG. 2, in other examples, sensing circuitry 204 may be in a separate housing from IMD 106 and may communicate with processor 210 via wired or wireless communication techniques. Example neural signals that sensing circuitry 204 may receive include, but are not limited to, a signal generated from local field potentials (LFPs) within one or more regions of brain 28. EEG and ECoG signals are examples of neural signals local field potentials that may be measured within brain 120. For instance, EEG signals may be sensed at the scalp, ECoG may be sensed at the cortical surface, and LFP may be sensed by electrodes implanted within the brain. However, local field potentials may include a broader genus of electrical signals within brain 120 of patient 112. Instead of, or in addition to, LFPs, IMD 106 may be configured to detect patterns of single-unit activity and/or multi-unit activity. IMD 106 may sample this activity at rates above 1,000 Hz, and in some examples within a frequency range of 6,000 Hz to 40,000 Hz. IMD 106 may identify the wave-shape of single units and/or an envelope of unit modulation that may be features used to differentiate or rank electrodes. In some examples, this technique may include phase-amplitude coupling to the envelope or to specific frequency bands in the LFPs sensed from the same or different electrodes.

Sensor 212 may include one or more sensing elements that sense values of a respective patient parameter. For example, sensor 212 may include one or more accelerometers, optical sensors, chemical sensors, temperature sensors, pressure sensors, or any other types of sensors. Sensor 212 may output patient parameter values that may be used as feedback to control delivery of therapy. IMD 106 may include additional sensors within the housing of IMD 106 and/or coupled via one of leads 114 or other leads. In addition, IMD 106 may receive sensor signals wirelessly from remote sensors via telemetry circuitry 208, for example. In some examples, one or more of these remote sensors may be external to the patient (e.g., carried on the external surface of the skin, attached to clothing, or otherwise positioned external to the patient). For example, IMD 106 may determine from these one or more additional sensors the brain state of the patient and sense signals for determining electrode movement during a brain state of lower fluctuation or lower noise to improve signal detection. In other examples, IMD 106 may employ an inertial sensor to determine when the patient is at rest (e.g., lying down and/or sleeping) and sense signals for determining lead movement during a time of rest to reduce noise or other motion artifacts in the sensed signals. In some examples, IMD 106 may sense signals for determining lead movement in response to receiving an indication that the patient received a dose of medication or the patient has entered a physician appointment.

Telemetry circuitry 208 supports, under the control of processor 210, wireless communication between IMD 106 and an external programmer 104 or another computing device. Processor 210 of IMD 106 may receive, as updates to programs, values for various stimulation parameters such as amplitude, pulse width, pulse rate and electrode combination, from programmer 104 via telemetry circuitry 208. The updates to the therapy programs may be stored within therapy programs 214 portion of memory 211. In addition, processor 210 may control telemetry circuitry 208 to transmit alerts or other information to programmer 104 that indicate a lead moved with respect to tissue. Telemetry circuitry 208 in IMD 106, as well as telemetry circuitry in other devices and systems described herein, such as programmer 104, may accomplish communication by radiofrequency (RF) communication techniques. In addition, telemetry circuitry 208 may communicate with external medical device programmer 104 via proximal inductive interaction of IMD 106 with programmer 104. Accordingly, telemetry circuitry 208 may send information to external programmer 104 on a continuous basis, at periodic intervals, or upon request from IMD 106 or programmer 104.

Power source 220 delivers operating power to various components of IMD 106. Power source 220 may include a small rechargeable or non-rechargeable battery and a power generation circuit to produce the operating power. Recharging may be accomplished through proximal inductive interaction between an external charger and an inductive charging coil within IMD 220. In some examples, power requirements may be small enough to allow IMD 220 to utilize patient motion and implement a kinetic energy-scavenging device to trickle charge a rechargeable battery. In other examples, traditional batteries may be used for a limited period of time.

Processor 210 may be an example of processing circuitry configured to perform the example techniques described in this disclosure. For example, processor 210 may receive a sensed signal (e.g., from sensing circuitry 204) sensed in a brain of a patient, where the sensed signal includes a neural signal and artifacts from a cardiac signal. Processor 210 may decompose the sensed signal into a plurality of components, each component having a plurality of frequencies. For instance, processor 210 may decompose the sensed signal into a plurality of BLIMFs (e.g., BLIMF1 to BLIMF10). In this example, BLIMF1 may include signal content from a first frequency to a second frequency of the sensed signal, BLIMF2 may include signal content from a third frequency to a fourth frequency of the sensed signal, and so forth.

Processor 210 may determine a first group of components, from the plurality of components, that are correlated with one another, the first group of components including two or more components. In one example of determining the first group of components, processor 210 may determine the first group of components as components of the sensed signal having amplitudes that increase or decrease at substantially the same time.

As one example, to determine the first group of components, from the plurality of components of the sensed signal, processor 210 may determine sets of adjacent components in the plurality of components. Each set of adjacent components may include sequential frequency bands. That is, the frequency band of BLIMF2 may sequentially follow the frequency band of BLIMF1, the frequency band of BLIMF3 may sequentially follow the frequency band of BLIMF2, and so forth. That is, the upper bound of BLIMF1 is a lower bound of BLIMF2, and so forth.

Processor 210 may determine a set of adjacent components from the set of adjacent components having a maximum correlation. As one example, processor 210 may determine a correlation value (e.g., a correlation coefficient, like Pearson's correlation) for each set of adjacent components, where the correlation value is indicative of an amount of correlation between each component of the set of adjacent components. Processor 210 may include the set of adjacent components having the maximum correlation in the first group of components. For example, processor 210 may determine which set of adjacent components has the maximum correlation value. Processor 210 may include the components that make up the set of adjacent components having the maximum correlation value in the first group of components.

In one or more examples, processor 210 may determine whether there are other components in the sensed signal that are correlated within a threshold to the components of the set of adjacent components having the maximum correlation. For instance, the set of adjacent components includes a first component and a second component. Processor 210 may determine components in the plurality of components of the sensed signal that correlate to at least one of the first component or the second component by a threshold value determined relative to the maximum correlation. For instance, if the maximum correlation value is 0.8, and a correlation threshold is 50%, processor 210 may determine components of the plurality of components of the sensed signal having a correlation value when correlated to the first component or the second component that is greater than 0.4 (e.g., 0.8*50%).

Processor 210 may determine an estimate of the cardiac signal based on the first group of components. As described above, the estimate of the cardiac signal includes the cardiac signal and components of the neural signal. For instance, because the first group of components are generated from components of the sensed signal that include both the cardiac signal (i.e., the artifact) and the neural signal, the estimate of the cardiac signal includes the cardiac signal and components of the neural signal.

Processor 210 may generate a denoised neural signal based on the estimate cardiac signal and a second group of components of the plurality of components. The cardiac signal is suppressed in the denoised neural signal, and the second group of components excludes the first group of components.

For example, as described in more detail below, the estimate of the cardiac signal includes the periodic artifacts generated from the cardiac signal that become artifacts in the sensed signal. Also, the amplitude of the cardiac signal may be relatively large in the estimate of the cardiac signal.

Accordingly, in one or more examples, processor 210 may determine local peaks in the estimate of the cardiac signal based on periodicity of peaks in the estimate of the cardiac signal. That is, peaks in the estimate of the cardiac signal that are periodic are more likely to be due to the cardiac signal than due to the neural signal.

Processor 210 may suppress the local peaks in the estimate of the cardiac signal to generate a suppressed cardiac signal. As one example, processor 210 may determine widths of each of the local peaks in the estimate of the cardiac signal, and set an amplitude across the width of each of the local peaks equal to zero. In this way, the cardiac signal may be removed (e.g., because the amplitude of the artifacts from the cardiac signal is set to zero), and the result is a suppressed cardiac signal. For example, the suppressed cardiac signal may be considered as the estimate of the cardiac signal with the cardiac signal removed. As explained, the estimate of the cardiac signal includes the cardiac signal and components of the neural signal. Therefore, by suppressing the cardiac signal in the estimate of the cardiac signal, the remaining signal is the components of the neural signal. In other words, the suppressed cardiac signal includes only the components of the neural signal.

The suppressed cardiac signal is based on the first group of components of the plurality of components of the sensed signal. There still exists the second group of components of the plurality of components of the sensed signal. However, as described above, the second group of components does not include the cardiac signal. Processor 210 may add the suppressed cardiac signal and the second group of components to form a resulting denoised neural signal. The denoised neural signal may be an accurate representation of the neural signal without the artifacts from the cardiac signal. That is, the cardiac signal may be suppressed in the denoised neural signal, where the cardiac signal was the signal causing artifacts in the sensed signal sensed in the brain of the patient.

Moreover, in some examples, processor 210 may utilize the estimate of the cardiac signal to determine parameters for the heart. For instance, as described above, because the peaks of the estimate of the ECG signal may be due to the ECG signal, differences between the peaks may be indicative of the R-R interval of the ECG signal of the heart. In this way, by utilizing electrodes implanted in brain 120 of patient 122, there may be a possibility to determine cardiac health without necessarily implanting electrodes near the heart. That is, a signal that is noise for the LFP signal can be extracted to determine cardiac health.

FIG. 3 is a block diagram of the external programmer 104 of FIG. 1 for controlling delivery of DBS therapy according to an example of the techniques of the disclosure. Although programmer 104 may generally be described as a hand-held device, programmer 104 may be a larger portable device or a more stationary device. In some examples, programmer 104 may be referred to as a tablet computing device. In addition, in other examples, programmer 104 may be included as part of a bed-side monitor, an external charging device or include the functionality of an external charging device. As illustrated in FIG. 3, programmer 104 may include a processor 310, memory 311, user interface 302, telemetry circuitry 308, and power source 320. Memory 311 may store instructions that, when executed by processor 310, cause processor 310 and external programmer 104 to provide the functionality ascribed to external programmer 104 throughout this disclosure. Each of these components may include electrical circuitry that is configured to perform some or all of the functionality described herein. For example, processor 310 may include processing circuitry configured to perform the processes discussed with respect to processor 310.

In general, programmer 104 comprises any suitable arrangement of hardware, alone or in combination with software and/or firmware, to perform the techniques attributed to programmer 104, and processor 310, user interface 302, and telemetry circuitry 308 of programmer 104. In various examples, programmer 104 may include one or more processors, which may include fixed function processing circuitry and/or programmable processing circuitry, as formed by, for example, one or more microprocessors, DSPs, ASICs, FPGAs, or any other equivalent integrated or discrete logic circuitry, as well as any combinations of such components. Programmer 104 also, in various examples, may include a memory 311, such as RAM, ROM, PROM, EPROM, EEPROM, flash memory, a hard disk, a CD-ROM, comprising executable instructions for causing the one or more processors to perform the actions attributed to them. Moreover, although processor 310 and telemetry circuitry 308 are described as separate modules, in some examples, processor 310 and telemetry circuitry 308 may be functionally integrated with one another. In some examples, processor 310 and telemetry circuitry 308 correspond to individual hardware units, such as ASICs, DSPs, FPGAs, or other hardware units.

Memory 311 (e.g., a storage device) may store instructions that, when executed by processor 310, cause processor 310 and programmer 104 to provide the functionality ascribed to programmer 104 throughout this disclosure. User interface 302 may include a button or keypad, lights, a speaker for voice commands, a display, such as a liquid crystal (LCD), light-emitting diode (LED), or organic light-emitting diode (OLED). In some examples the display may be a touch screen. User interface 302 may be configured to display any information related to the delivery of stimulation therapy, identified patient behaviors, sensed patient parameter values, patient behavior criteria, or any other such information. User interface 302 may also receive user input via user interface 302. The input may be, for example, in the form of pressing a button on a keypad or selecting an icon from a touch screen.

Telemetry circuitry 308 may support wireless communication between IMD 106 and programmer 104 under the control of processor 310. Telemetry circuitry 308 may also be configured to communicate with another computing device via wireless communication techniques, or direct communication through a wired connection. In some examples, telemetry circuitry 308 provides wireless communication via an RF or proximal inductive medium. In some examples, telemetry circuitry 308 includes an antenna, which may take on a variety of forms, such as an internal or external antenna. In some examples, IMD 106 and/or programmer 104 may communicate with remote servers via one or more cloud-services in order to deliver and/or receive information between a clinic and/or programmer.

Examples of local wireless communication techniques that may be employed to facilitate communication between programmer 104 and IMD 106 include RF communication according to the 802.11 or Bluetooth specification sets or other standard or proprietary telemetry protocols. In this manner, other external devices may be capable of communicating with programmer 104 without needing to establish a secure wireless connection.

Processor 310 may be an example of processing circuitry configured to perform the example techniques described in this disclosure. For example, processor 310 may receive a sensed signal (e.g., from processor 210 of IMD 106) including artifacts from a cardiac signal that is sensed in a brain of a patient. Processor 310 may decompose the sensed signal into a plurality of components, each component having a plurality of frequencies. Processor 310 may determine a first group of components, from the plurality of components, that are correlated with one another, the first group of components including two or more components. Processor 310 may determine an estimate of the cardiac signal based on the first group of components. Processor 310 may generate a denoised neural signal based on the estimated cardiac signal and a second group of components of the plurality of components. The cardiac signal is suppressed in the denoised neural signal, and the second group of components excludes the first group of components.

Moreover, in some examples, processor 310 may utilize the estimate of the cardiac signal to determine parameters for the heart. For instance, as described above, because the peaks of the estimate of the ECG signal may be due to the ECG signal, difference between the peaks may be indicative of the R-R interval of the ECG signal of the heart. In this way, by utilizing electrodes implanted in brain 120 of patient 122, there may be a possibility to determine cardiac health without necessarily implanting electrodes near the heart. That is, a signal that is noise for the LFP signal can be extracted to determine cardiac health.

FIGS. 4A-4J are graphs illustrating examples of a sensed signal decomposed into a plurality of components. Processing circuitry (e.g., processor 210 or processor 310) may be configured to receive a sensed signal sensed in a brain of a patient (e.g., from sensing circuitry 204), where the sensed signal includes a neural signal and artifacts from a cardiac signal. The processing circuitry may decompose the sensed signal into a plurality of components of the sensed signal, each component having a plurality of frequencies. For instance, FIGS. 4A-4J illustrate components 400A-400J. Each one of components 400A-400J is a component of the plurality of components of the sensed signal. Also, in the example of FIGS. 4A-4J, each component of the plurality of components is a component in the time-domain instead of frequency domain.

As one example, component 400A may be an example of a first BLIMF having a plurality of frequencies that includes frequencies between a first frequency and a second frequency. Component 400B may be an example of a second BLIMF having a plurality of frequencies that includes frequencies between a third frequency and a fourth frequency, and so forth. Each component has a center frequency, and includes more frequencies, and not only the center frequency. The sum of the components 400A-400J may be equivalent to the sensed signal. In the example of FIGS. 4A-4J, there are ten components.

In some examples, the sensed signal may be in a frequency range of 0 Hz to 125 Hz. Accordingly, in the example of FIGS. 4A-4J, each component may be centered around a frequency of 12.5 Hz steps (e.g., 6.25 Hz, 18.75 Hz, 31.25 Hz, and so forth). There may be various ways in which to generate the example signals illustrated in FIGS. 4A-4J. As one example, the processing circuitry (e.g., processor 210 or 310) may perform a Hilbert transform. The processing circuitry may then perform a variational mode decomposition (VMD) using Tikhonov Regularization and/or Elasticnet Regression. The result may be the example BLIMFs 400A-400J illustrated in FIGS. 4A-4J.

FIGS. 5A-5J are graphs illustrating examples of the graphs of the plurality of components of FIGS. 4A-4J squared. FIGS. 6A-6J are graphs illustrating examples of the graphs of FIGS. 5A-5J convolved with a triangular function. For instance, for processing, the processing circuitry may multiply the plurality of components of FIGS. 4A-4J by itself (e.g., multiply component 400A by component 400A to generate a signal representing a square of component 400A). FIGS. 5A-5J illustrate signals 500A-500J, where signal 500A represents the square of component 400A, signal 500B represents the square of component 500B, and so forth. FIGS. 6A-6J illustrate signals 600A-600J, where signal 600A represents signal 500A convolved with a triangular function, signal 600B represents signal 600B convolved with a triangular function (e.g., the same triangular function), and so forth.

The example operations illustrated with respect to FIGS. 5A-5J and FIGS. 6A-6J are provided as an example, and should not be considered as necessary in all examples. The processing circuitry may perform other operations to ease with processing components 400A-400J, or may perform operations with components 400A-400J without further processing components 400A-400J.

FIG. 7 is a conceptual diagram illustrating information indicative of correlation between the plurality of components that are generated by decomposing of the sensed signal. For instance, FIG. 7 illustrates map 700, which forms a two-dimensional grid. The x-axis of map 700 represents each of the components of the sensed signal (e.g., components 400A-400J, signal 500A-500J, or signal 600A-600J). The y-axis of map 700 also represents each of the components of the sensed signal (e.g., components 400A-400J, signal 500A-500J, or signal 600A-600J). For ease, the example of FIG. 7 is described with respect to components 400A-400J (e.g., each component of the plurality of components that was generated by decomposing the sensed signal).

The gray-scale in the two-dimensional grid formed by map 700 represents the amount of correlation (e.g., correlation value) between two of the components. A grid point with a lighter color represents high correlation (e.g., correlation value close to 1) between the component corresponding to the grid point, and a grid point with a darker color represents low correlation (e.g., correlation value close to 0) between the corresponding components.

For example, the grid point located at (1, 10) in map 700 represents the correlation between component 400A and 400J. The grid point located at (7, 7) in map 700 represents the correlation between 400G and 400G (e.g., self-correlation).

FIG. 7 illustrates a way in which the processing circuitry (e.g., processor 210 or processor 310) may determine a first group of components, from the plurality of components of the sensed signal, that are correlated with one another. For instance, the processing circuitry may determine correlation between component 400A and components 400B-400J (e.g., determine respective correlation values), determine correlation between component 400B and components 400C-400J, and so forth. In some examples, rather than repeating operations of determining correlation values for each of the components of the sensed signal, the processing circuitry may limit determining correlation values to components of the sensed signal having a center frequency that is less than a maximum center frequency (e.g., truncate the number of components that are evaluated to those having a center maximum center frequency less than a maximum center frequency).

The processing circuitry may determine sets of adjacent components in the plurality of components, where each set of adjacent components includes sequential, adjacent frequency bands. For instance, component 400A and component 400B may be adjacent components if the frequencies in the frequency band of component 400B numerically follow the frequencies in the frequency band of component 400A, and there is no other component having frequencies in a frequency band that is within the frequency band of component 400A and component 400B. Again, as described above, each of components 400A-400J includes signal components of a plurality of frequencies that form a frequency band centered around a center frequency.

In the example of FIG. 7, components 400A and 400B are adjacent, components 400B and 400C are adjacent, and so forth. The processing circuitry may determine a set of adjacent components from the set of adjacent components having a maximum correlation. For instance, the processing circuitry may determine that a correlation value of components 400D and 400E is greater than a correlation value of any other adjacent components. As an example, the correlation value of components 400D and 400E may be 0.8. In this example, the processing circuitry may include components 400D and 400E in the first group of components, where, as described above, the first group of components are components of the sensed signal that are correlated with one another, and where the first group of components includes two or more components of the sensed signal.

The processing circuitry may also determine components in the plurality of components that correlate to at least one of component 400D (e.g., the first component) or component 400E (e.g., the second component) by a threshold value determined relative to the maximum correlation. For instance, the threshold value may be 50% of the maximum correlation value (e.g., 0.8), and the correlation value indicative of the correlation between component 400D and 400E. In this example, the processing circuitry may include components in the first group of components having a correlation value that is greater than the threshold. For example, assume that the correlation value indicative of the correlation between component 400I and component 400D is 0.6. In this case, the processing circuitry may include component 400I in the first group of components because 0.6 is greater than (0.8*50%). However, assume that the correlation value indicative of the correlation between component 400B and component 400D is 0.3. In this case, the processing circuitry may not include component 400B in the first group of components because 0.3 is less than (0.8*50%).

In this way, the processing circuitry may determine a first group of components, from the plurality of components of the sensed signal, that are correlated with one another. The cause of the correlation of the components in the first group of components may be due to the periodicity of the cardiac signal, which is the artifact in the sensed signal that is to be removed to determine the actual neural signal from the sensed signal. The second group of components (e.g., the components of the sensed signal that are not in the first group of components) may not be correlated with one another because the cardiac signal may not include components having frequency bands of the components of the second group of components of the sensed signal.

By determining the first group of components, the processing circuitry may isolate the components in the sensed signal that include the artifacts from the cardiac signal.

However, the first group of components still include components of the neural signal. That is, the signal content of the first group of components includes the cardiac signal and components of the neural signal, whereas the signal content of the second group of components includes components of the neural components, and may not include components of the cardiac signal.

Therefore, the first group of components may represent an estimate of a cardiac signal. For instance, the processing circuitry may determine an estimate of the cardiac signal based on the first group of components (e.g., by summing the first group of components). FIG. 8 is a graph illustrating an example of an estimate of a cardiac signal that is noise in the sensed signal generated based on the correlation between the plurality of components. However, because the estimate of the cardiac signal is based on the first group of components (e.g., summation of the components of the first group of components), and the first group of components includes the cardiac signal and components of the neural signal, the estimate of the cardiac signal includes the cardiac signal and components of the neural signal.

In accordance with one or more examples described in this disclosure, after the processing circuitry determines the estimate of the cardiac signal (e.g., by summing the components of the first group of components), the processing circuitry may determine the actual cardiac signal within the estimate of the cardiac signal. Stated another way, the processing circuitry may start with the sensed signal. From the sensed signal, the processing circuitry may isolate the components of the sensed signal that include the cardiac signal to form an estimate of the cardiac signal. From the estimate of the cardiac signal, the processing circuitry (e.g., processor 210 or 310) may identify the cardiac signal, so that the processing circuitry can squelch the cardiac signal. The result would then be a first group of components, having the cardiac signal removed, that can be summed with the second group of components to determine a denoised neural signal (e.g., the sensed signal with the artifacts from the cardiac signal removed).

FIG. 9A is a graph illustrating the graph of FIG. 8 squared. In one or more examples, the peaks in the estimate of the cardiac signal, as illustrated in FIG. 8, such as peaks that are periodic may represent the signal content of the cardiac signal. In one example, as an option, the processing circuitry (e.g., processor 210 or processor 310) may square the estimate of the cardiac signal to enhance the peaks, and FIG. 9A illustrates an example of the estimate of the cardiac signal of FIG. 8 squared (e.g., estimate of the cardiac signal multiplied by itself).

FIG. 9B is a graph illustrating estimated peaks of the graph of FIG. 9A. For instance, the circles in the FIG. 9B highlight the peaks from the graph of FIG. 9A. However, not all peaks in FIG. 9A may be considered as estimates of peaks used for suppressing the artifacts from the cardiac signal. As an example, to qualify as an estimated peak used for suppressing the artifacts from the cardiac signal, there may be certain criteria to satisfy. One example of the criteria may be that the amplitude of the signal content be greater than a threshold. Another example of the criteria may be that there is a minimum separation between two peaks. If there is another "peak" (e.g., because amplitude is sufficient high), but this other peak follows an earlier peak, then the other peak may not be considered as an estimated peak that is used for suppressing the artifacts from the cardiac signal.

For instance, FIG. 9B illustrates points 900A, 900B, 900C, and 900D. In one example, the processing circuitry may determine that point 900A corresponds to a peak that is used for suppressing the artifacts from the cardiac signal. However, the processing circuitry may determine that point 900B does not correspond to a peak that is used for suppressing the artifacts from the cardiac signal. For instance, point 900B may be less than an artifact detection threshold (e.g., the amplitude of point 900B is less than a threshold that indicates that point 900B is a peak). In some examples, the processing circuitry may determine that point 900B and 900C are not peaks because these points are less than a minimum separation from point 900A. As one example, a findpeak function may be utilized in which the findpeak function looks for the highest peak with a minimum separation distance, and in this example, does not identify points 900B and 900C as peaks. In a successive step, the processing circuitry may identify a second peak in the surrounding of each first peak found by findpeak.

One example for why there may be a minimum separation between two peaks is because of minimum R-R intervals in a cardiac signal. For instance, the R-R interval in a cardiac signal may be indicative of the amount of polarization-depolarization of a heart (e.g., intervals between successive heartbeats). There tends to be a minimum R-R interval. Therefore, if there is a peak that is within an R-R interval, then it is likely that the peak is not due to the cardiac signal, but possibly some other source. As one example, the minimum separation amount may be approximately 600 milliseconds (ms). For instance, within a time window of 2 seconds, the processing circuitry may identify a maximum of three peaks (e.g., 2000 ms divided by 600 ms).

FIG. 9C is a graph illustrating the estimated peaks in the graph of FIG. 8 based on the estimated peaks in the graph of FIG. 9B. For instance, FIG. 9C illustrates the estimated cardiac signal of FIG. 8 with the estimated peaks identified in FIG. 9B superimposed. As illustrated, FIG. 9C includes the estimated ECG, which is an example of the cardiac signal.

FIG. 10 is a graph illustrating a concatenation of a plurality of time windows of the estimate of the cardiac signal, including the estimate of the cardiac signal of FIG. 8 and the estimated peaks of FIG. 9C. For instance, FIG. 8 illustrates one time window of the estimated cardiac signal (e.g., 2000 ms). There may be additional time windows of the cardiac signal following and/or preceding the time window of the estimate of the cardiac signal illustrated in FIG. 8. In one or more examples, the processing circuitry may perform similar operations such as those described in the FIGS. 9A-9C to determine estimates of peaks in the time windows that follow and/or precede the time window of the estimate of the cardiac signal of FIG. 8. FIG. 10 illustrates the concatenation of the plurality of time windows (e.g., 7000 ms rather than 2000 ms of FIG. 8), including circles showing peaks.

FIG. 11 is a graph illustrating the graph of FIG. 10 with removal of false positives. As described above with FIG. 10, in one or more examples, the processing circuitry may estimate peaks in each of the time windows, and then concatenate the time windows. In such cases, after concatenation, there may be a possibility that some of the identified peaks are not actual peaks that should be used for suppressing the cardiac signal. As one example, after concatenation, there may be peaks that are separated by less than the minimum separation amount. For instance, at the borders of time windows, there is a higher likelihood that a peak is identified, but should not be identified, because that peak is separated by less than the minimum separation amount. FIG. 11 illustrates the examples where such peaks, that are false positives, are removed from the example of FIG. 10.

By utilizing the example techniques described, such as with respect to FIGS. 8-11, the processing circuitry may determine the peaks of the signal content that is from the cardiac signal, and create the artifacts in the sensed signal. For example, the processing circuitry may determine local peaks in the estimate of the cardiac signal based on the periodicity of peaks in the estimate of the cardiac signal. The processing circuitry may then suppress the local peaks in the estimate of the cardiac signal to generate a suppressed cardiac signal (e.g., a signal in which the cardiac signal is suppressed). The processing circuitry may generate the denoised neural signal (e.g., the sensed signal with the cardiac signal suppressed) based on the suppressed cardiac signal.

For instance, the processing circuitry may determine the suppressed cardiac signal based on the first group of components of the plurality of components of the sensed signal. The processing circuitry may sum the suppressed cardiac signal with the second group of components of the plurality of components of the sensed signal to generate the denoised neural signal.

However, in some examples, to suppress the cardiac signal in the sensed signal, the processing circuitry may also determine the width of the signal content that is from the cardiac signal. That is, to suppress the local peaks, such as those of FIG. 11, the processing circuitry may determine the widths of each of the local peaks, and set an amplitude across the width of each of the local peaks substantially equal to zero (e.g., absolute value is less than 5 microvolts).

The width of the local peaks may be indicative of the time instances in the sensed signal where the artifacts from the cardiac signal are present in the sensed signal. By setting the width of the local peaks substantially equal to zero in the components of the sensed signal in which the cardiac signal is present, the processing circuitry may effectively remove (e.g., suppress) the cardiac signal.

For instance, FIG. 11 illustrates the estimate the cardiac signal, and includes the peaks of the signal content that are due to the cardiac signal. However, as described, the estimate of the cardiac signal includes both the cardiac signal and components of the neural signal. To suppress the cardiac signal, the processing circuitry may also determine the width of the signal content of the cardiac signal that caused the peak to be detected. The width may be estimated by a threshold crossing or by an auto-adjusting threshold detection.

In some examples, instead of or in addition to using zero-crossing (e.g., threshold crossing), the processing circuitry may utilize half-prominence peaks. For example, the peak of the signal content may be in the center of two points of the signal content (e.g., a first point and a second point). The first point and the second point may be points in the signal content have half prominence of the peak that is in the center of the first point and the second point. The width of the peak may be defined by the time between the first point and the second point.

FIG. 12 is a graph illustrating example peaks for determining information of a cardiac signal. As described above, in one or more examples, the processing circuitry may be configured to determine the cardiac signal that is present in the sensed signal so that the processing circuitry can suppress (e.g., remove) the cardiac signal from the sensed signal, and generate a denoised neural signal.

However, in one or more examples, it may be possible for the processing circuitry to leverage the sensed signal to determine cardiac health, such as by evaluating the peaks in the estimate of the cardiac signal. For instance, FIG. 12 illustrates an example of all the peaks identified in the estimate of the cardiac signal, such as that of FIG. 10. In one or more examples, the temporal distance between the peaks may be indicative of a parameter of the cardiac signal. As one example, the temporal distance between the peaks may be indicative of the R-R interval of the heart.

In this way, the processing circuitry may determine parameters (e.g., R-R interval) of the cardiac signal based on the sensed signal. That is, although the cardiac signal is a noise artifact in the sensed signal, the processing circuitry may utilize the noise artifact to determine parameters of the cardiac signal based on the sensed signal. Accordingly, it may be possible to determine parameters of the cardiac signal without needing to implant electrodes or leads that are proximate to the heart. Instead, it may be possible to determine parameters of the cardiac signal based on electrodes and leads implanted within the brain of the patient.

FIG. 13 is a graph illustrating an example of the R-R interval of the heart of the patient. For instance, FIG. 13 illustrates an example of the R-R interval that the processing circuitry may determine from the cardiac signal based on the sensed signal. For instance, the time intervals between peaks in FIG. 12 may be indicative of the R-R interval, and FIG. 13 illustrates a plurality of R-R intervals measured over a period of time.

The following describes FIGS. 14A-14F. FIGS. 14A-14F conceptually illustrate the example techniques described in this disclosure to suppress the cardiac signal from the sensed signal to generate a denoised neural signal, where the cardiac signal is suppressed in the denoised neural signal.

FIG. 14A is a graph illustrating an example of a sensed signal that includes artifacts from a cardiac signal that is sensed in a brain of a patient. For instance, FIG. 14A illustrates an example of the signal that sensing circuitry 204 may sense.

FIG. 14B is a graph illustrating an example of a sum of a first group of components of a plurality of components of the sensed signal that form an estimate of the cardiac signal that includes components of the neural signal. For instance, the processing circuitry (e.g., processor 210 or processor 310) may decompose the sensed signal into a plurality of components of the sensed signal, each component having a plurality of frequencies. As an example, the processing circuitry may determine BLIMF1 to BLIMFN. Examples of BLIMF1 to BLIMFN include examples from FIGS. 4A-4J, such as when there are ten components. Each of BLIMF1 to BLIMFN includes signal content of the sensed signal over a narrow frequency band, centered at respective centered frequencies. In one or more examples, the summation of BLIMF1 to BLIMFN may be the same as the sensed signal illustrated in FIG. 14A.

The processing circuitry may determine the first group of components, from the plurality of components of the sensed signal, that are correlated with one another. The first group of components may include two or more components. As one example, the processing circuitry may determine sets of adjacent components in the plurality of components, where each set of adjacent components includes sequential frequency bands. The processing circuitry may determine a set of adjacent components from the set of adjacent components having a maximum correlation. For instance, as described above with respect to FIG. 7, the processing circuitry may determine a respective correlation value for BLIMF1 and BLIMF2, BLIMF1 and BLIMF3, and so forth, a respective correlation value for BLIMF2 and BLIMF3, BLIMF 2 and BLIMF4, and so forth, and so forth for BLIMF3 to BLIMFN.

For each set of adjacent components, the processing circuitry may determine which set of adjacent components has the highest correlation vale (e.g., indicative of the maximum correlation). The processing circuitry may include the set of adjacent components having the maximum correlation in the first group of components. The set of adjacent components having the maximum correlation may include a first component and a second component. In one or more examples, the processing circuitry may determine components in the plurality of components that correlate to at least one of the first component or the second component by a threshold value determined relative to the maximum correlation (e.g., greater than 50% of the greatest correlation value) and include the determined components in the first group of components.

As described, the components in the first group of components are correlated with one another. The cause of the correlation may be due to the periodicity of the cardiac signal. Hence, the first group of components may include the signal content from the cardiac signal, but also include components of the neural signal. A second group of components of the plurality of components of the sensed signal that excludes the components of the first group of components may not be correlated with other components. This may be because the second group of components includes signal content of the neural signal, and not the cardiac signal. The neural signal tends not be periodic, and therefore, not correlated.

The example of FIG. 14B illustrates a summation of the components in the first group of components. For instance, assume there are ten components (e.g., BLIMF1 to BLIMF10) of the sensed signal. Assume that each one of BLIMF1 to BLIMF10 corresponds to respective ones of FIGS. 4A-4J (e.g., BLIMF1 is FIG. 4A, BLIMF2 is FIG. 4B, and so forth). In this example, assume that the first group of components includes BLIMF2-BLIMF6 (e.g., FIGS. 4B, 4C, 4D, 4E, and 4F). FIG. 14B is the summation of BLIMF2-BLIMF6.

FIG. 14B may be considered as an example of an estimate of the cardiac signal. That is, the processing circuitry may determine an estimate of the cardiac signal based on the first group of components (e.g., by summing the components of the first group of components). As described above, the estimate of the cardiac signal includes both the cardiac signal and components of the neural signal. For instance, each one of BLIMF2-BLIMF6 includes both the cardiac signal and the neural signal. However, the cardiac signal may dominate in content due to the higher amplitude and energy of the cardiac signal. Therefore, although the cardiac signal may be dominant in the estimate of the cardiac signal, the estimate of the cardiac signal includes the cardiac signal and components of the neural signal.

In one or more examples, the processing circuitry may be configured to generate a denoised neural signal based on the estimate of the cardiac signal and a second group of components of the plurality of components of the sensed signal. The cardiac signal is suppressed in the denoised neural signal, and the second group of components excludes the first group of components. An example of the denoised neural signal is illustrated in FIG. 14F, and described below. The second group of components of the plurality of components of the sensed signal may be components of the sensed signal that are not correlated with other components, and may exclude components of the first group of components.

FIG. 14C is a graph illustrating an example of peak detection and width estimation of the cardiac signal components in the estimate of the cardiac signal that includes components of the neural signal. To generate the denoised neural signal, the processing circuitry may determine the contribution of the cardiac signal in the estimate of the cardiac signal. For instance, the processing circuitry may determine the local peaks and width of various portions of the estimate of the cardiac signal, as illustrated in FIG. 14C. For example, the processing circuitry may perform the example operations described above with respect to FIGS. 9A-11 to determine the local peaks. The processing circuitry may determine the width of a cardiac component of the signal in the estimate of the cardiac signal, as described above. In FIG. 14C, the local peaks are illustrated with circles, and the width of the cardiac component of the cardiac signal is illustrated with a bolded line.

FIG. 14D is a graph illustrating an example of the suppression of the local peaks from the example of FIG. 14C. For instance, the processing circuitry may set the amplitude value across the width of each of the local peaks substantially equal to zero. For instance, the processing circuitry may determine local peaks in the estimate of the cardiac signal based on periodicity of peaks in the estimate of the cardiac signal, as illustrated in FIG. 14C. The processing circuitry may suppress the local peaks in the estimate of the cardiac signal to generate a suppressed cardiac signal.

FIG. 14D illustrates an example of the suppressed cardiac signal. For instance, the suppressed cardiac signal may be a signal in which the cardiac signal is suppressed, and the remaining signal may be components of the neural signal. One example way to suppress the cardiac signal is for the processing circuitry to determine widths of each of the local peaks, as illustrated in FIG. 14C, and set the amplitude across the width of each of the local peaks substantially equal to zero (e.g., within ±1 uV). In one or more examples, to generate the denoised neural signal, as illustrated in FIG. 14F, the processing circuitry may sum the second group of components and the suppressed cardiac signal to generate the denoised neural signal.

FIG. 14E is a graph illustrating an example of a sum of a second group of components of the sensed signal that excludes the first group of components. For instance, as described above, as an example, the first group of components may include BLIMF2-BLIMF6. In this example, the second group of components may include BLIMF1 and BLIMF7-BLIMF10. The example of FIG. 14E may be considered as a summation of the BLIMF1 and BLIMF7-BLIMF10 components.

FIG. 14F is a graph illustrating an example of the sum of the graphs of FIG. 14E and FIG. 14D showing a sensed signal having the artifacts from the cardiac signal removed. For instance, as described above, to generate the denoised signal, the processing circuitry may sum the second group of components and the suppressed cardiac signal. FIG. 14E is an example of a sum of the second group of components, and FIG. 14D is an example of the suppressed cardiac signal (e.g., signal with the cardiac signal suppressed, so that the remaining signal is components of the neural signal). FIG. 14F is the sum of FIG. 14E and FIG. 14D, and illustrates the denoised neural signal. That is, FIG. 14F illustrates an example of the artifacts from the cardiac signal being suppressed in the sensed signal that is sensed in the brain of the patient, so that the remaining signal is the actual neural signal.

FIG. 15 is a graph illustrating power versus frequency of a sensed signal including artifacts from a cardiac signal and a sensed signal having artifacts from the cardiac signal removed. In the example of FIG. 15, line 1500 illustrates the power versus frequency of the sensed signal including artifacts from the cardiac signal, and line 1502 illustrates the power versus frequency of the sensed signal having artifacts from the cardiac signal removed, so that the remaining signal is the actual neural signal (i.e., denoised neural signal). As can be seen, the power of the sensed signal with the cardiac signal artifacts (e.g., combination of the cardiac signal and neural signal) is substantially greater than the power of the denoised neural signal. In one or more examples, using the power of the sensed signal without denoising may result in a determination of higher power in a frequency band of interest than the amount of actual power that may be present in the neural signal within the frequency band of interest. With the example techniques described in this disclosure, the processing circuitry may denoise the sensed signal so that the actual neural signal is used for therapy delivery or diagnosis.

FIG. 16 is a flowchart illustrating an example technique according to one or more examples described in this disclosure. For ease of illustration, the example of FIG. 16 is described with respect to processing circuitry. Examples of the processing circuitry include one or combination of processor 210 and processor 310 alone or in combination with the other components of IMD 106 or programmer 104.

Processing circuitry may receive a sensed signal that is sensed in a brain of a patient, where the sensed signal includes a neural signal and artifacts from a cardiac signal (1600). For instance, processor 210 may receive the sensed signal from sensing circuitry 204, which receives the sensed signal from electrodes 116, 118. As another example, rather than processor 210 preforming the operations, processor 310 may receive the sensed signal from transmission from IMD 106. As one example, the sensed signal comprises a sensed local field potential (LFP), and the cardiac signal comprises an electrocardiogram (ECG) signal (e.g., that is sensed as part of the LFP signal and is an artifact on the sensed LFP signal).

The processing circuitry may decompose the sensed signal into a plurality of components, each component having a plurality of frequencies (1602). For example, each component is a time-varying signal (e.g., in the time domain) that includes a plurality of frequencies, such that when each component is summed together (e.g., all are summed together), the result is the original sensed signal. For instance, the processing circuitry may decompose the sensed signal into a plurality of components, with each component having different spectral content contained in a narrow frequency band. There may be some overlap of spectral content between components but not full overlap. Examples of the plurality of components of the sensed signal that the processing circuitry decomposes the sensed signal into include the examples in FIGS. 4A-4J.

The processing circuitry may determine a first group of components, from the plurality of components, that are correlated with one another (1604). The first group of components may include two or more components. For example, determining the first group of components may include determining components of the sensed signal having amplitudes that increase or decrease at substantially the same time. For instance, to determine the first group of components, from the plurality of components of the sensed signal, the processing circuitry may determine sets of adjacent components in the plurality of components, where each set of adjacent components includes sequential frequency bands. The processing circuitry may determine a set of adjacent components from the set of adjacent components having a maximum correlation. For instance, the processing circuitry may determine correlation values, as illustrated in FIG. 7, for sets of components, and determine the set of adjacent components having the maximum correlation value.

The processing circuitry may include the set of adjacent components having the maximum correlation in the first group of components. For instance, the set of adjacent components may include a first component and a second component, and the processing circuitry may include the first component and the second component in the first group of components. In addition, in some examples, the processing circuitry may also determine components in the plurality of components that correlate to at least one of the first component or the second component by a threshold value determined relative to the maximum correlation. As an example, the processing circuitry may determine if the correlation value of a component of the plurality of components and the first component or the second component (e.g., the components that formed the set of components having the maximum correlation value) is greater than 50% of the maximum correlation value. The processing circuitry may include the determined components in the first group of components.

The processing circuitry may determine an estimate of the cardiac signal based on the first group of components (1606). For example, the processing circuitry may sum the first group of components to generate the estimate of the cardiac signal. FIGS. 8, 11, and 14B are examples of the estimate of the cardiac signal.

The processing circuitry may generate a denoised neural signal based on the estimate of the cardiac signal and a second group of components of the plurality of components (1608). The second group of components excludes the first group of components. In accordance with one or more examples, the cardiac signal is suppressed in the denoised neural signal. In this manner, the remaining signal, including the second group of components and excluding the first group of components, is a denoised LFP signal.

For example, the processing circuitry may determine local peaks in the estimate of the cardiac signal based on periodicity of peaks in the estimate of the cardiac signal, and suppress the local peaks in the estimate of the cardiac signal to generate a suppressed cardiac signal. One example of the suppressed cardiac signal is FIG. 14D. In one or more examples, to generate the denoised neural signal, the processing circuitry may sum the second group of components (e.g., as illustrated in FIG. 14E) and the suppressed cardiac signal (e.g., as illustrated in FIG. 14D) to generate the denoised neural signal (e.g., as illustrated in FIG. 14F). In some examples, to suppress the local peaks, the processing circuitry may determine a width of each of the local peaks, and set an amplitude across the width of each of the local peaks substantially equal to zero.

The following describe example techniques that may be used together or separately.

Example 1. A method for artifact suppression in a sensed signal, the method comprising: receiving, with processing circuitry, the sensed signal sensed in a brain of a patient, wherein the sensed signal includes a neural signal and artifacts from a cardiac signal; decomposing, with the processing circuitry, the sensed signal into a plurality of components of the sensed signal, each component having a plurality of frequencies; determining, with the processing circuitry, a first group of components, from the plurality of components of the sensed signal, that are correlated with one another, the first group of components including two or more components of the sensed signal; determining, with the processing circuitry, an estimate of the cardiac signal based on the first group of components, wherein the estimate of the cardiac signal includes the cardiac signal and components of the neural signal; and generating, with the processing circuitry, a denoised neural signal based on the estimate of the cardiac signal and a second group of components of the plurality of components of the sensed signal, wherein the cardiac signal is suppressed in the denoised neural signal, and wherein the second group of components excludes the first group of components.

Example 2. The method of example 1, further comprising: determining therapy parameters for deep brain stimulation (DBS) based on the denoised neural signal.

Example 3. The method of any of examples 1 and 2, wherein determining the estimate of the cardiac signal comprises summing the first group of components to generate the estimate of the cardiac signal.

Example 4. The method of any of examples 1-3, further comprising: determining local peaks in the estimate of the cardiac signal based on periodicity of peaks in the estimate of the cardiac signal; and suppressing the local peaks in the estimate of the cardiac signal to generate a suppressed cardiac signal, wherein generating the denoised neural signal comprises summing the second group of components and the suppressed cardiac signal.

Example 5. The method of example 4, wherein suppressing the local peaks comprises: determining widths of each of the local peaks; and setting amplitude across the width of each of the local peaks substantially equal to zero.

Example 6. The method of any of examples 1-5, wherein determining the first group of components, from the plurality of components of the sensed signal comprises: determining sets of adjacent components in the plurality of components, wherein each set of adjacent components includes sequential frequency bands; determining a set of adjacent components from the set of adjacent components having a maximum correlation; and including the set of adjacent components having the maximum correlation in the first group of components.

Example 7. The method of example 6, wherein the set of adjacent components includes a first component and a second component, the method further comprising: determining components in the plurality of components that correlate to at least one of the first component or the second component by a threshold value determined relative to the maximum correlation; and including the determined components in the first group of components.

Example 8. The method of any of examples 1-7, wherein determining the first group of components comprises determining components of the sensed signal having amplitudes that increase or decrease at substantially the same time.

Example 9. The method of any of examples 1-8, wherein the neural signal comprises a sensed local field potential (LFP) that includes the artifacts from the cardiac signal.

Example 10. The method of any of examples 1-9, further comprising: determining parameters of the cardiac signal based on the sensed signal.

Example 11. A system for artifact suppression in a sensed signal, the system comprising: memory; and processing circuitry coupled to the memory and configured to: receive the sensed signal sensed in a brain of a patient, wherein the sensed signal includes a neural signal and artifacts from a cardiac signal; decompose the sensed signal into a plurality of components of the sensed signal, each component having a plurality of frequencies; determine a first group of components, from the plurality of components of the sensed signal, that are correlated with one another, the first group of components including two or more components of the sensed signal; determine an estimate of the cardiac signal based on the first group of components, wherein the estimate of the cardiac signal includes the cardiac signal and components of the neural signal; and generate a denoised neural signal based on the estimate of the cardiac signal and a second group of components of the plurality of components of the sensed signal, wherein the cardiac signal is suppressed in the denoised neural signal, and wherein the second group of components excludes the first group of components.

Example 12. The system of example 11, further comprising an implantable medical device (IMD), wherein the IMD includes the processing circuitry.

Example 13. The system of example 12, wherein the IMD further comprises sensing circuitry configured to sense the sensed signal.

Example 14. The system of any of examples 11 and 12, wherein the processing circuitry is configured to determine therapy parameters for deep brain stimulation (DBS) based on the denoised neural signal.

Example 15. The system of any of examples 11-14, wherein to determine the estimate of the cardiac signal, the processing circuitry is configured to sum the first group of components to generate the estimate of the cardiac signal.

Example 16. The system of any of examples 11-15, wherein the processing circuitry is configured to: determine local peaks in the estimate of the cardiac signal based on periodicity of peaks in the estimate of the cardiac signal; and suppress the local peaks in the estimate of the cardiac signal to generate a suppressed cardiac signal, wherein to generate the denoised neural signal, the processing circuitry is configured to sum the second group of components and the suppressed cardiac signal.

Example 17. The system of example 16, wherein to suppress the local peaks, the processing circuitry is configured to: determine widths of each of the local peaks; and set amplitude across the width of each of the local peaks substantially equal to zero.

Example 18. The system of any of examples 11-17, wherein to determine the first group of components, from the plurality of components of the sensed signal, the processing circuitry is configured to: determine sets of adjacent components in the plurality of components, wherein each set of adjacent components includes sequential frequency bands; determine a set of adjacent components from the set of adjacent components having a maximum correlation; and include the set of adjacent components having the maximum correlation in the first group of components.

Example 19. The system of example 18, wherein the set of adjacent components includes a first component and a second component, and wherein the processing circuitry is configured to: determine components in the plurality of components that correlate to at least one of the first component or the second component by a threshold value determined relative to the maximum correlation; and include the determined components in the first group of components.

Example 20. The system of any of examples 11-19, wherein to determine the first group of components, the processing circuitry is configured to determine components of the sensed signal having amplitudes that increase or decrease at substantially the same time.

Example 21. The system of any of examples 11-20, wherein the neural signal comprises a sensed local field potential (LFP) that includes the artifacts from the cardiac signal.

Example 22. The system of any of examples 11-21, wherein the processing circuitry is configured to: determine parameters of the cardiac signal based on the sensed signal.

Example 23. A computer-readable storage medium comprising instructions that when executed cause one or more processors to: receive a sensed signal sensed in a brain of a patient, wherein the sensed signal includes a neural signal and artifacts from a cardiac signal; decompose the sensed signal into a plurality of components of the sensed signal, each component having a plurality of frequencies; determine a first group of components, from the plurality of components of the sensed signal, that are correlated with one another, the first group of components including two or more components of the sensed signal; determine an estimate of the cardiac signal based on the first group of components, wherein the estimate of the cardiac signal includes the cardiac signal and components of the neural signal; and generate a denoised neural signal based on the estimate of the cardiac signal and a second group of components of the plurality of components of the sensed signal, wherein the cardiac signal is suppressed in the denoised neural signal, and wherein the second group of components excludes the first group of components.

The techniques described in this disclosure may be implemented, at least in part, in hardware, software, firmware or any combination thereof. For example, various aspects of the described techniques may be implemented within one or more processors, such as fixed function processing circuitry and/or programmable processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), ferroelectric RAM (FRAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method for artifact suppression in a sensed signal, the method comprising:

receiving, with processing circuitry, the sensed signal sensed in a brain of a patient, wherein the sensed signal includes a neural signal and artifacts from a cardiac signal;

decomposing, with the processing circuitry, the sensed signal into a plurality of components of the sensed signal, each component having a plurality of frequencies;

determining, with the processing circuitry, a first group of components, from the plurality of components of the sensed signal, that are correlated with one another, the first group of components including two or more components of the sensed signal, wherein determining the first group of components comprises:

determining sets of adjacent components in the plurality of components, wherein each set of adjacent components includes sequential frequency bands, wherein the sets of adjacent components comprises at least a first set of two components having sequential frequency bands and a second set of two components having sequential frequency bands;

determining a set of adjacent components from the sets of adjacent components having a maximum correlation, wherein the set of adjacent components includes a first component and a second component, and wherein a frequency band of the second component immediately follows a frequency band of the first component;

determining components in the plurality of components that correlate to at least one of the first component or the second component by a threshold value determined relative to the maximum correlation; and including the determined components in the first group of components;

determining, with the processing circuitry, an estimate of the cardiac signal based on the first group of components, wherein the estimate of the cardiac signal includes the cardiac signal and components of the neural signal;

generating, with the processing circuitry, a denoised neural signal based on the estimate of the cardiac signal and a second group of components of the plurality of components of the sensed signal, wherein the cardiac signal is suppressed in the denoised neural signal, and wherein the second group of components excludes the first group of components; and causing, with the processing circuitry, delivery of deep brain stimulation (DBS) therapy based on the denoised neural signal.

2. The method of claim 1, further comprising:

determining therapy parameters for the DBS therapy based on the denoised neural signal.

3. The method of claim 1, wherein determining the estimate of the cardiac signal comprises summing the first group of components to generate the estimate of the cardiac signal.

4. The method of claim 1, further comprising:

determining local peaks in the estimate of the cardiac signal based on periodicity of peaks in the estimate of the cardiac signal; and suppressing the local peaks in the estimate of the cardiac signal to generate a suppressed cardiac signal, wherein generating the denoised neural signal comprises summing the second group of components and the suppressed cardiac signal.

5. The method of claim 4, wherein suppressing the local peaks comprises:

determining widths of each of the local peaks; and setting amplitude across the width of each of the local peaks substantially equal to zero.

6. The method of claim 4, wherein determining the local peaks comprises determining the local peaks based on the periodicity of peaks and a distance between two consecutive local peaks being greater than a minimum distance.

7. The method of claim 1, wherein determining the first group of components comprises determining components of the sensed signal having amplitudes that increase or decrease at substantially the same time.

8. The method of claim 1, wherein the neural signal comprises a sensed local field potential (LFP) that includes the artifacts from the cardiac signal.

9. The method of claim 1, further comprising:

determining parameters of the cardiac signal based on the sensed signal.

10. The method of claim 1, wherein determining the first group of components comprises determining the first group of components from the plurality of components limited to components having a center frequency less than a threshold center frequency.

11. A system for artifact suppression in a sensed signal, the system comprising:

memory; and processing circuitry coupled to the memory and configured to:

receive the sensed signal sensed in a brain of a patient, wherein the sensed signal includes a neural signal and artifacts from a cardiac signal;

decompose the sensed signal into a plurality of components of the sensed signal, each component having a plurality of frequencies;

determine a first group of components, from the plurality of components of the sensed signal, that are correlated with one another, the first group of components including two or more components of the sensed signal, wherein to determine the first group of components, the processing circuitry is configured to:

determine sets of adjacent components in the plurality of components, wherein each set of adjacent components includes sequential frequency bands, wherein the sets of adjacent components comprises at least a first set of two components having sequential frequency bands and a second set of two components having sequential frequency bands;

determine a set of adjacent components from the sets of adjacent components having a maximum correlation, wherein the set of adjacent components includes a first component and a second component, and wherein a frequency band of the second component immediately follows a frequency band of the first component;

determine components in the plurality of components that correlate to at least one of the first component or the second component by a threshold value determined relative to the maximum correlation; and include the determined components in the first group of components;

determine an estimate of the cardiac signal based on the first group of components, wherein the estimate of the cardiac signal includes the cardiac signal and components of the neural signal;

generate a denoised neural signal based on the estimate of the cardiac signal and a second group of components of the plurality of components of the sensed signal, wherein the cardiac signal is suppressed in the denoised neural signal, and wherein the second group of components excludes the first group of components; and cause delivery of deep brain stimulation (DBS) therapy based on the denoised neural signal.

12. The system of claim 11, further comprising an implantable medical device (IMD), wherein the IMD includes the processing circuitry.

13. The system of claim 12, wherein the IMD further comprises sensing circuitry configured to sense the sensed signal.

14. The system of claim 11, wherein the processing circuitry is configured to determine therapy parameters for the DBS therapy based on the denoised neural signal.

15. The system of claim 11, wherein to determine the estimate of the cardiac signal, the processing circuitry is configured to sum the first group of components to generate the estimate of the cardiac signal.

16. The system of claim 11, wherein the processing circuitry is configured to:

determine local peaks in the estimate of the cardiac signal based on periodicity of peaks in the estimate of the cardiac signal; and suppress the local peaks in the estimate of the cardiac signal to generate a suppressed cardiac signal, wherein to generate the denoised neural signal, the processing circuitry is configured to sum the second group of components and the suppressed cardiac signal.

17. The system of claim 16, wherein to suppress the local peaks, the processing circuitry is configured to:

determine widths of each of the local peaks; and set amplitude across the width of each of the local peaks substantially equal to zero.

18. The system of claim 16, wherein to determine the local peaks, the processing circuitry is configured to determine the local peaks based on the periodicity of peaks and a distance between two consecutive local peaks being greater than a minimum distance.

19. The system of claim 11, wherein to determine the first group of components, the processing circuitry is configured to determine components of the sensed signal having amplitudes that increase or decrease at substantially the same time.

20. The system of claim 11, wherein the neural signal comprises a sensed local field potential (LFP) that includes the artifacts from the cardiac signal.

21. The system of claim 11, wherein the processing circuitry is configured to:

determine parameters of the cardiac signal based on the sensed signal.

22. The system of claim 11, wherein to determine the first group of components, the processing circuitry is configured to determine the first group of components from the plurality of components limited to components having a center frequency less than a threshold center frequency.

23. A non-transitory computer-readable storage medium comprising instructions that when executed cause one or more processors to:

receive a sensed signal sensed in a brain of a patient, wherein the sensed signal includes a neural signal and artifacts from a cardiac signal;

decompose the sensed signal into a plurality of components of the sensed signal, each component having a plurality of frequencies;

determine a first group of components, from the plurality of components of the sensed signal, that are correlated with one another, the first group of components including two or more components of the sensed signal, wherein the instructions that cause the one or more processors to determine the first group of components comprise instructions that cause the one or more processors to:

determine sets of adjacent components in the plurality of components, wherein each set of adjacent components includes sequential frequency bands, wherein the sets of adjacent components comprises at least a first set of two components having sequential frequency bands and a second set of two components having sequential frequency bands;

determine a set of adjacent components from the sets of adjacent components having a maximum correlation, wherein the set of adjacent components includes a first component and a second component, and wherein a frequency band of the second component immediately follows a frequency band of the first component;

determine components in the plurality of components that correlate to at least one of the first component or the second component by a threshold value determined relative to the maximum correlation; and include the determined components in the first group of components;

determine an estimate of the cardiac signal based on the first group of components, wherein the estimate of the cardiac signal includes the cardiac signal and components of the neural signal;

generate a denoised neural signal based on the estimate of the cardiac signal and a second group of components of the plurality of components of the sensed signal, wherein the cardiac signal is suppressed in the denoised neural signal, and wherein the second group of components excludes the first group of components;

cause delivery of deep brain stimulation (DBS) therapy based on the denoised neural signal.

* * * * *